(12) United States Patent
Radhakrishnan et al.

(10) Patent No.: US 10,688,039 B2
(45) Date of Patent: Jun. 23, 2020

(54) SCAVENGING DISSOLVED OXYGEN VIA ACOUSTIC DROPLET VAPORIZATION

(71) Applicant: UNIVERSITY OF CINCINNATI, Cincinnati, OH (US)

(72) Inventors: Kirthi Radhakrishnan, Cincinnati, OH (US); Christy K. Holland, Cincinnati, OH (US); Kevin J. Haworth, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 15/754,077

(22) PCT Filed: Aug. 26, 2016

(86) PCT No.: PCT/US2016/048934
§ 371 (c)(1),
(2) Date: Feb. 21, 2018

(87) PCT Pub. No.: WO2017/035454
PCT Pub. Date: Mar. 2, 2017

(65) Prior Publication Data
US 2018/0303750 A1 Oct. 25, 2018

Related U.S. Application Data

(60) Provisional application No. 62/210,056, filed on Aug. 26, 2015.

(51) Int. Cl.
*A61N 7/00* (2006.01)
*A61K 9/00* (2006.01)
(Continued)

(52) U.S. Cl.
CPC ............ *A61K 9/0009* (2013.01); *A61K 9/107* (2013.01); *A61K 31/02* (2013.01); *A61K 47/24* (2013.01);
(Continued)

(58) Field of Classification Search
None
See application file for complete search history.

(56) References Cited

U.S. PATENT DOCUMENTS 3,055,805 A 9/1962 Nahas
5,840,276 A 11/1998 Apfel
(Continued)

OTHER PUBLICATIONS

Kevin J. Haworth et al, "Ultrasound-Mediated Scavenging of Dissolved Oxygen"; Apr. 22, 2015, p. 1, XP055557577, ULR:https://cctst.uc.edu/sites/defult/files/2015/Haworth%20Trans%20Sci%20Conf%20Poster.pdf.
(Continued)

*Primary Examiner* — Jonathan Cwern
(74) *Attorney, Agent, or Firm* — Dinsmore & Shohl LLP

(57) ABSTRACT

Methods and compositions for treating a patient for a condition characterized by an excess blood concentration of dissolved gas in at least one targeted region of the patient are provided. The method comprises administering a composition comprising a perfluorocarbon droplet emulsion into the blood of the patient; insonifying the at least one target region sufficient to achieve formation of microbubbles by droplet vaporization of at least a portion of the perfluorocarbon droplets present in the blood; whereby a concentration gradient favoring movement of gas molecules from the blood into the microbubbles is established for a time frame.

17 Claims, 12 Drawing Sheets

(51) Int. Cl.
  *A61K 47/24*   (2006.01)
  *A61K 9/107*   (2006.01)
  *A61K 31/02*   (2006.01)
  *A61K 47/69*   (2017.01)
  *A61B 8/08*    (2006.01)
  *G01N 33/49*   (2006.01)

(52) U.S. Cl.
  CPC .......... *A61K 47/6925* (2017.08); *A61B 8/481* (2013.01); *A61N 2007/0039* (2013.01); *G01N 33/4925* (2013.01)

(56) References Cited

U.S. PATENT DOCUMENTS

| | | | |
|---|---|---|---|
| 2008/0221382 A1* | 9/2008 | Karshafian | ............... A61N 5/10 600/2 |
| 2010/0076095 A1 | 3/2010 | Thomas et al. | |
| 2010/0267842 A1 | 10/2010 | Kiral et al. | |
| 2011/0177005 A1 | 7/2011 | Rapoport et al. | |
| 2013/0330389 A1 | 12/2013 | Fabiilli et al. | |

OTHER PUBLICATIONS

Extended European Search Report for corresponding EP App. 16840197.4 dated Feb. 26, 2019.

International Search Report and Written Opinion of corresponding PCT/US2016048934 dated Nov. 18, 2016.

Radhakrishan et al, Scavenging dissolved oxygen via acoustic droplet vaporization; The Journal of the Acoustical Society of America, vol. 136, 2014 (retrieved on Oct. 19, 2016) http://scitation.aip.org/content/asa/journal/asa/136/4/10.121/1.

Radhakrishan et al, Scavenging dissolved oxygen via acoustic droplet vaporization; Ultrasonics Sonochemistry, Jul. 2016; Retrieved from the internet Oct. 20, 2016 at https://www.researchgate.net/publication/295548832_Scavenging_dissolved_oxygen_via_acoustic_droplet_vaporization.

Liu et al, CO2 gas induced drug release from pH-sensitive liposome to circumvent doxorubicin resistant cells; Chemical Communications, vol. 48, 2012.

Mercado, Karla P. et al, "Size-isolation of ultrasound-mediated phase change perfluorocarbon droplets using differential centrifugation"; J. Acoust. Soc. Am. 139 (5), May 2016, pp. EL142-EL148.

* cited by examiner

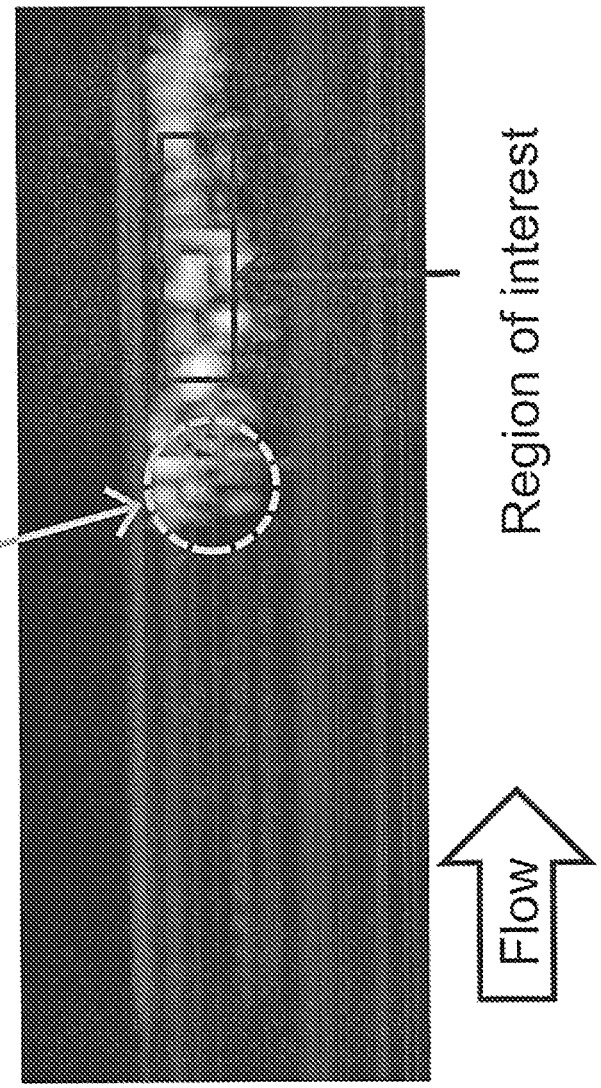

Fig. 5B

SCAVENGING DISSOLVED OXYGEN VIA ACOUSTIC DROPLET VAPORIZATION

CROSS-REFERENCE TO RELATED APPLICATIONS

This application is a U.S. National Stage Application under § 371 of International Application No. PCT/US2016/048934, filed Aug. 26, 2016, and claims priority under 35 U.S.C. § 119(e) to U.S. Provisional Application Ser. No. 62/210,056, filed Aug. 26, 2015, which applications are hereby incorporated by reference in their entirety.

STATEMENT REGARDING FEDERALLY SPONSORED RESEARCH OR DEVELOPMENT

This invention was made with government support under TR000078 awarded by National Institutes of Health. The government has certain rights in the invention.

BACKGROUND OF THE INVENTION

The phenomenon of acoustic droplet vaporization (ADV), the acoustically mediated phase transition of liquid perfluorocarbon droplet emulsions into gas bubbles, is under investigation for several biomedical applications. For example, submicron-sized perfluorocarbon droplets extravasate from leaky tumor vessels, undergo ADV, and provide contrast on ultrasound images of cancerous tissue. ADV-induced microbubbles generated from micron-sized droplets have also been investigated as point targets for phase aberration correction. Further, contrast-enhanced photoacoustic images have been created using ADV to trigger the localized release of cardiogreen dye from a perfluoropentane (PFP) double emulsion. ADV is also being explored for various direct and adjuvant therapeutic applications. Micron-sized perfluorocarbon microbubbles created via ADV have been shown to occlude capillary beds and arterioles, which can facilitate embolotherapy in cancer treatment. Previous studies have also demonstrated ADV-mediated delivery of chemotherapeutic drugs such as paclitaxel, chlorambucil, and doxorubicin loaded in perfluorocarbon droplets. Thermal ablation of cancerous lesions has been enhanced using perfluorocarbon droplets as cavitation nuclei during high intensity focused ultrasound (HIFU) exposure. Further, ADV microbubbles can provide contrast-enhanced image guidance during treatment. More recently, perfluorocarbon droplets have been shown to lower the acoustic power needed for HIFU-mediated lysis of blood clots relative to HIFU exposure without droplets. Spatiotemporally-controlled ADV-mediated drug release from perfluorocarbon double emulsions has also been shown to regulate the mechanical properties of tissue-engineered scaffolds.

Several studies have reported that ADV results in a significant volumetric expansion of the perfluorocarbon. For example, the ideal gas law was previously used to predict a volumetric expansion of a factor of 125 (i.e., a radial expansion of 5). The measured volumetric expansion of evaporating perfluoropentane was a factor of 151 (i.e., a radial expansion factor of 5.3), and the computed radial expansion was a factor of 5.9, which accounts for the diffusion of gases into and out of the microbubbles. From these results and other studies, the amount of ingassing and thus the expansion factor appear to depend on the experimental conditions. The diffusion of gases into perfluorocarbon-based ultrasound contrast agents has also been discussed in other studies, while the high solubility of oxygen in perfluorochemicals and the use of perfluorochemicals as blood substitute agents have been demonstrated in previous studies.

Although studies have demonstrated that dissolved gases in a fluid can diffuse in and out of perfluorocarbon droplets, the need exists to develop therapeutic methods of utilizing the phenomenon of ultrasound-mediated gas diffusion concomitant with the cavitation nucleation associated with ADV as a strategy to scavenge gases in situ.

SUMMARY

It is understood that both the following summary and the detailed description are exemplary and explanatory and are intended to provide further explanation of the disclosure as claimed. Neither the summary nor the description that follows is intended to define or limit the scope of the disclosure to the particular features mentioned in the summary or description.

Utilization of the phenomenon of ultrasound-mediated gas diffusion concomitant with the cavitation nucleation associated with ADV can potential serve as a strategy to scavenge gases in situ. Accordingly, it is an object of the present invention to provide a method of treating a patient for a condition characterized by an excess blood concentration of dissolved gas in at least one targeted region of the patient. In some embodiments, the method includes administering a composition comprising a perfluorocarbon droplet emulsion into the blood of the patient and insonifying the at least one target region sufficient to achieve formation of microbubbles by droplet vaporization of at least a portion of the perfluorocarbon droplets present in the blood, whereby a concentration gradient favoring movement of gas molecules from the blood into the microbubbles is established for a time frame.

In another embodiment, a method for releasing a pharmaceutical agent from a pH-sensitive delivery vehicle comprising the pharmaceutical agent to a target region of a patient is provided. In some embodiments, the method includes administering the delivery vehicle comprising the pharmaceutical agent into the blood of the patient; administering a composition comprising a perfluorocarbon droplet emulsion into the blood of the patient; and isonifying the target region sufficient to achieve formation of microbubbles by droplet vaporization of at least a portion of the perfluorocarbon droplets present in the blood; whereby a concentration gradient favoring movement of carbon dioxide molecules from the blood into the microbubbles is established for a time frame sufficient to reduce pH of the blood in the target region and cause release of the pharmaceutical agent from the delivery vehicle to the target region.

In another embodiment, a pharmaceutical composition comprising perfluorocarbon droplets is provided, wherein the volume parameters of the droplets is determined prior to administration to a patient in accordance with the patient's blood concentration of an undesirable gas and the amount of gas sought to be removed from blood present in a target region of the patient.

BRIEF DESCRIPTION OF THE DRAWINGS

FIG. 1 shows the in vitro flow system to measure changes in dissolved oxygen (DO) in a fluid during ADV. PFP droplets diluted in air-saturated PBS were infused into the flow system and insonified by the 2 MHz transducer with an aperture of 6.3 cm and a focal distance of 6.4 cm. DO sensors placed upstream and downstream of the insonation were used to quantify changes in DO of the fluid during ADV. The imaging array was used to confirm the formation of microbubbles during ADV. The effluent collected from the flow system was used to quantify the size distribution of droplets in the absence and presence of ultrasound exposure.

FIG. 2. Determination of the acoustic droplet vaporization threshold. FIG. 2A shows B-mode image of EVA tubing containing PFP droplets exposed to 4.9 MPa peak rarefactional pressure ultrasound pulses. The mean gray scale value within the region of interest demarcated in red was quantified as the downstream echogenicity after ADV.

FIG. 3. Size distribution of effluent droplets from flow system.

FIG. 4 shows percent dissolved oxygen (DO) relative to air-saturated phosphate buffered saline (PBS) measured in the absence of droplets (black bars), measured upstream of the insonation region in the presence of non-centrifuged droplets (tan bars), and measured downstream of the insonation in the presence of non-centrifuged droplets (orange bars) as a function of the ultrasound peak rarefactional pressure. Error bars indicate the standard deviation of three measurements. The violet bars indicate the predicted DO after ultrasound exposure of non-centrifuged droplets. The predicted DO values are not statistically different from the DO measured downstream of the insonation region. Error bars indicate the propagated error based on the standard deviations from FIG. 3A and equation 6.

FIG. 5. Calculated size distribution of droplets surviving one pass through the lung. FIG. 5B shows the measured volume-weighted number-density size distribution of non-centrifuged PFP droplets (solid black) and calculated volume-weighted number-density size distribution of non-centrifuged PFP droplets that survive one pass through pulmonary capillaries (dashed black). Measured volume-weighted number-density size distribution of PFP droplets centrifuged at 9 g for 5 min (solid red) and calculated volume-weighted number-density size distribution of centrifuged PFP droplets that survive one pass through pulmonary capillaries (dashed red).

FIG. 6. Size distribution of centrifuged droplets and their oxygen scavenging effect.

FIG. 7. Dissolved oxygen change as a function of concentration for a monodisperse droplet distribution.

DETAILED DESCRIPTION

Figure 1:
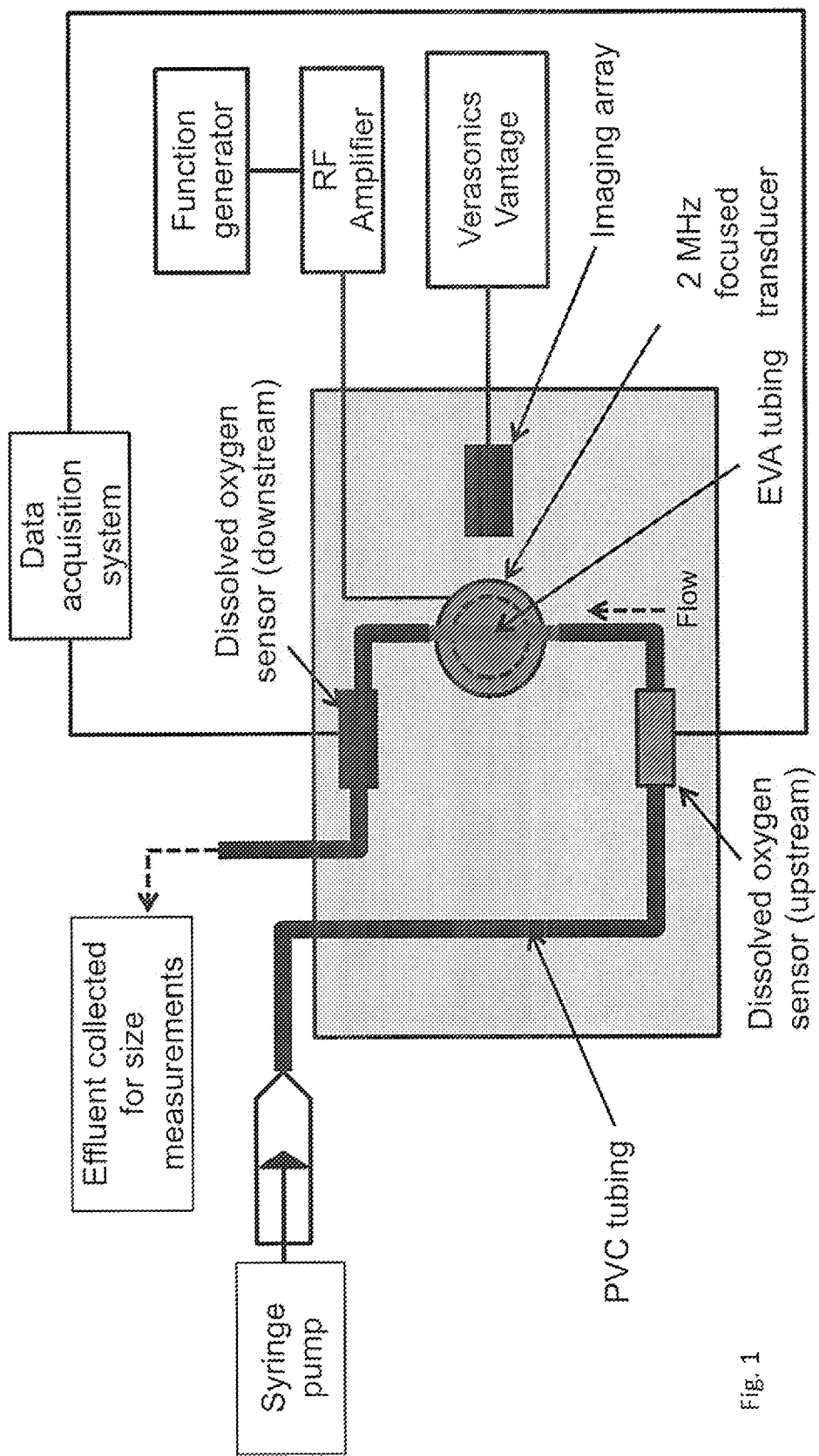
FIG. 1. Experimental setup.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the compositions or processes are described as using specific materials or an order of individual steps, it is appreciated that materials or steps may be interchangeable such that the description of the invention may include multiple parts or steps arranged in many ways as is readily appreciated by one of skill in the art.

The terminology used herein is for describing particular aspect only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

This presently disclosed data relates to the acoustic droplet vaporization (ADV) of perfluorocarbon emulsions, and the potential of this process to serve as an ultrasound-mediated gas scavenging technology. Perfluoropentane droplets diluted in phosphate-buffered saline (PBS) were insonified by a 2 MHz transducer at peak rarefactional pressures lower than and greater than the ADV pressure amplitude threshold in an in vitro flow phantom. The change in dissolved oxygen (DO) of the PBS before and after ADV was measured. A numerical model of gas scavenging, based on conservation of mass and equal partial pressures of gases at equilibrium, was developed. At insonation pressures exceeding the ADV threshold, the DO of air-saturated PBS decreased with increasing insonation pressures, dropping as low as 25% of air saturation within 20 s. The decrease in DO of the PBS during ADV was dependent on the volumetric size distribution of the droplets and the fraction of droplets transitioned during ultrasound exposure. Numerically predicted changes in DO from the model agreed with the experimentally measured DO, indicating that concentration gradients can explain this phenomenon. Using computationally modified droplet size distributions that would be suitable for in vivo applications, the DO of the PBS was found to decrease with increasing concentrations. This data demonstrates that ADV can significantly decrease the DO in an aqueous fluid, which may have direct therapeutic applications and should be considered for ADV-based diagnostic or therapeutic application.

Accordingly, the presently-disclosed subject matter includes a method of treating a patient for a condition characterized by an excess blood concentration of dissolved gas in at least one targeted region of the patient. In embodiments, the method comprises: administering a composition comprising a perfluorocarbon droplet emulsion into the blood of the patient; insonifying the at least one target region sufficient to achieve formation of microbubbles by droplet vaporization of at least a portion of the perfluorocarbon droplets present in the blood; whereby a concentration gradient favoring movement of gas molecules from the blood into the microbubbles is established for a time frame.

The term "droplet" as used herein refers to an amount of liquid that is encased or surrounded by a different, enclosing substance. Droplets that are less than one micrometer in size are commonly referred to as "nanodroplets" and those that are in the one micrometer to tens or hundreds of micrometers in size are commonly referred to as "microdroplets." If a droplet is encased in another liquid, the droplet and its casing may also be referred to as an "emulsion" or a "droplet emulsion." An emulsion is a mixture of two immiscible liquids. Emulsions are colloids wherein both phases of the colloid (i.e., the dispersed phase and the continuous phase) are liquids and one liquid (the dispersed phase or encapsulated material) is dispersed/encapsulated in the other liquid (the continuous phase or encapsulating material). The dispersed phase liquid can be, as is often with perfluorocarbons, referred to as taking the form of "particles" suspended in the continuous phase liquid. Each use of the term "particle" or "particles" herein is intended to apply to liquid perfluorocarbon microspheres or droplets in the continuous liquid phase and microbubbles (which make the emulsion in such state a colloidal suspension). The term "bubble" as used herein refers to a bubble of gas encased or surrounded by an encapsulating substance. Bubbles that are from one micrometer to several tens or hundreds of micrometers in size are commonly referred to as "microbubbles", while bubbles that are smaller than one micrometer in size are commonly referred to as "nanobubbles."

In embodiments, the administered perfluorocarbon droplet emulsion includes a dispersed liquid phase (i.e. encapsulated material) of a perfluorocarbon. Perfluorocarbons are known to be chemically and biologically inert substances which are capable of dissolving very large volumes of gases, including oxygen and carbon dioxide, at concentrations much larger than water, saline, and plasma. In addition, perfluorocarbons can transport these gases to diffuse across distances. In embodiments, generally no specific limitation on suitable perfluorocarbons is necessary other than suitable vapor pressure. Non-limiting examples of suitable perfluorocarbons for use in the administered perfluorocarbon droplet emulsion include perfluoroalkanes such as perfluoropentane, perfluorohexane, perfluorononane, perfluorohexyl bromide, perfluorooctyl bromide, and perfluorodecyl bromide; perfluoroalkyl ethers; perfluoroalkenes such as bisperfluorobutylethylene; perfluorocycloalkanes such as perfluorodecalin, perfluorocyclohexanes, perfluoroadamantane, perfluorobicyclodecane, and perfluoromethyl decahydroquinoline; perfluoro amines such as perfluoroalkyl amines; and $C_1$-$C_8$ substituted compounds thereof, isomers thereof, and combinations thereof. Depending on the particular application, the volatility, vapor pressure, and/or boiling point of the perfluorocarbon can affect performance and suitability. Generally, for mammal in vivo applications, a boiling point greater than about 37° C. such as over about 50° C. can be desirable. However, perfluorocarbons with boiling points greater than room temperature (25° C.) can also be utilized. Further, increased long-term stability of micelles can often be realized by choosing a perfluorocarbon having a boiling point which is substantially higher, such as greater than about 120° C. The perfluorocarbon in the emulsion droplets can be present as a single perfluorocarbon compound or a mixture of such compounds. In some cases, a mixture of perfluorocarbon compounds can allow for optimization or customization of boiling temperature and control of droplet to bubble transitions. The content of perfluorocarbon in the emulsion can vary depending on the particular species chosen for each component.

In some embodiments, the dispersed liquid phase of the administered perfluorocarbon droplet emulsion further includes an emulsion stabilizer, as are known in the art. Exemplary emulsion stabilizers include poly(ethylene) oxide block copolymers.

In embodiments, the administered perfluorocarbon droplet emulsion includes a continuous liquid phase (i.e. encapsulating material). The encapsulating material can include a lipid, protein, polymer, gel, surfactant, peptide, or sugar, as is known in the art.

Although some embodiments of the perfluorocarbon droplet emulsions can consist essentially of a dispersed liquid phase perfluorocarbon and a continuous liquid phase encapsulating material (and optionally an emulsion stabilizer), other additives can be optionally included. Suitable additives for the perfluorocarbon droplet emulsions can include, but are not limited to, hydrogels, anti-oxidants, sequestering agents, chelating agents, steroids, anti-coagulants, drugs, carriers, solvents, preservatives, surfactants, wetting agents, and combinations thereof. The administered perfluorocarbon droplet emulsions can also include excipients such as solubility-altering agents (e.g. ethanol, propylene glycol, and sucrose) and polymers (e.g. polycaprylactones and PLGA's), as well as pharmaceutically active compounds.

A wide variety of approaches known in the art can be useful for preparing the perfluorocarbon droplet emulsions, including techniques such as sonication, agitation, mixing, high shear agitation, homogenization/atomization, and the like. An exemplary process for preparing the perfluorocarbon droplet emulsions can include causing the perfluorocarbon to condense into a liquid and then extruding or emulsifying the perfluorocarbon liquid into or in the presence of an encapsulating material to form a droplet emulsion comprising a dispersed liquid phase perfluorocarbon and a continuous liquid phase encapsulating material. To condense the perfluorocarbon, the perfluorocarbon may be cooled to a temperature below the phase transition temperature of the perfluorocarbon having the lowest boiling point, compressed to a pressure above the phase transition pressure of the perfluorocarbon having the highest phase transition pressure value, or a combination of the two. The contents of the perfluorocarbon droplet emulsion may be entirely or primarily in the liquid phase.

In some embodiments of a method of treating a patient for a condition characterized by an excess blood concentration of dissolved gas in at least one targeted region of the patient, the method further comprises preparation of a perfluorocarbon droplet emulsion prior to the step of administration, wherein preparation comprises generation of size-isolated perfluorocarbon droplets. In some embodiments, the size-isolated perfluorocarbon droplets are generated by differential centrifugation. In other embodiments, the size-isolated perfluorocarbon droplets are generated by microfluidic techniques. In some embodiments, the size of the generated perfluorocarbon droplets ranges from 0.3 µm to about 100 µm. In other embodiments, the size of the generated perfluorocarbon droplets ranges from about 2 µm to about 5 µm diameter.

In embodiments of a method of treating a patient for a condition characterized by an excess blood concentration of dissolved gas in at least one targeted region of the patient, the administered perfluorocarbon droplet emulsions can be caused to expand into a bubble (including a microbubble) of encapsulated perfluorocarbon gas, by a process referred to as "activation". In some embodiments, the perfluorocarbon droplet emulsions are considered metastable, as they are stable as droplet emulsions and do not spontaneously expand into bubbles without additional energy. For example, in some embodiments exposure of the administered perfluorocarbon droplet emulsions to body temperature is not by itself is not enough to cause them activate and expand into microbubbles. Additional activation energy is required. In embodiments, the administered perfluorocarbon droplet emulsions have an activation energy that is low enough for use in human therapeutics or treatment.

In some embodiments, the perfluorocarbon droplet emulsions are acoustically activatable, and the method of activation is known as acoustic droplet vaporization, or ADV. In ADV, the droplet is subjected to ultrasonic energy sufficient to cause the liquid within the droplet to change phase and become a gas. This causes the perfluorocarbon emulsion droplet to become a bubble or microbubble of encapsulated perfluorocarbon gas, with a corresponding increase in size. In embodiments, the ultrasonic energy may be provided by a medical ultrasound transceiver. Thus, some embodiments of a method of treating a patient for a condition characterized by an excess blood concentration of dissolved gas in at least one targeted region of the patient include insonifying the at least one target region sufficient to achieve formation of microbubbles by droplet vaporization. The administered perfluorocarbon emulsions can be insonified (e.g. with ultrasonic energy) by use of a medical ultrasound transceiver. In some embodiments, isonifying comprises administering ultrasound to the target at or above a threshold pressure amplitude, wherein "threshold" is defined as a minimum pressure amplitude necessary to transition the droplets. In some embodiments, the isonifying comprises administering from between 500 kHz to 10 MHz ultrasound and ultrasound is administered at a pressure amplitude between the threshold pressure and 5 MPa. In other embodiments, the isonifying comprises administering 2 MHz ultrasound and the threshold pressure amplitude is about 1.7 MPa.

This insonification of the perfluorocarbon droplet emulsions creates a perfluorocarbon microbubble undersaturated with dissolved gases, and thereby a concentration gradient favoring movement of the excess dissolved gas molecules from the blood into the microbubbles is established for a time frame. The concentration differential results in the excess dissolved gas molecules moving from the blood into the perfluorocarbon microbubble, thereby scavenging the excess dissolved gas from the blood. In embodiments, the established concentration gradient is calculated to achieve sufficient, but not excess, removal of dissolved gas from the target region. In some embodiments, the calculation is according to a model comprising variables selected from: identity of the gas sought to be removed, blood concentration of the gas sought to be removed, solubility of the gas in both blood and the microbubbles, size of perfluorocarbon droplets, fraction of the perfluorocarbon droplets transitioned into microbubbles due to ultrasound insonation, radial expansion coefficient of the perfluorocarbon droplets that transition into microbubbles, and insonation pressure. In some embodiments, the concentration gradient is favoring movement of the excess dissolved gas molecules from the blood into the microbubbles established for a time frame of between approximately 10 milliseconds and approximately 60 seconds. In other embodiments, the concentration gradient is established for a time from of approximately 20 seconds.

Eventually the microbubbles with the scavenged gas will dissolve, releasing the scavenged gas back into the blood. In the case of scavenged oxygen, the released scavenged oxygen will likely either bind to hemoglobin or increase the dissolved oxygen content of plasma. This dissolution is anticipated to happen on a time scale of tens of seconds. Blood circulates through the adult human body approximately once per minute. As the blood circulates through the pulmonary capillary bed, the dissolved oxygen in the blood would return to normal oxygen levels and the perfluorocarbon microbubbles would be exhaled similar to the excretion of other perfluorocarbon-based ultrasound contrast agent gases.

Similarly, a pharmaceutical composition comprising perfluorocarbon droplets is provided, wherein the volume parameters of the droplets is determined prior to administration to a patient in accordance with the patient's blood concentration of undesirable gas and the amount of gas sought to be removed from blood present in a target region of the patient. In certain embodiments, the perfluorocarbon droplets are size-isolated droplets. The perfluorocarbon droplets in the pharmaceutical composition are as previously described herein.

The instantly disclosed pharmaceutical compositions and methods can be used to scavenge a variety of excess dissolved gas molecules in the blood and can be used to treat a variety of conditions. As used herein, the term "treating" relates to any treatment of a condition characterized by an excess blood concentration of dissolved gas in at least one targeted region of the patient, including but not limited to prophylactic therapeutic treatment. "Treating" includes any effect, e.g., lessening, reducing, modulating, or eliminating, that results in the improvement of the condition characterized by an excess blood concentration of dissolved gas in at least one targeted region of the patient. Topical administration is one way of administering the instant composition comprising the perfluorocarbon droplet emulsion to the patient in the disclosed methods of treating a patient for a condition characterized by an excess blood concentration of dissolved gas in at least one targeted region of the patient. Topical administration can include application of the composition comprising the perfluorocarbon droplet emulsion to the skin or mucous membranes of a subject. In embodiments, topical administration of the composition comprising the perfluorocarbon droplet emulsion is application of the composition to the epidermis of a subject. The administering of the composition comprising the perfluorocarbon droplet emulsion can also be performed, for example, intravenously or intra-arterially. A "patient" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like).

In some embodiments of a method of treating a patient for a condition characterized by an excess blood concentration of dissolved gas in at least one targeted region of the patient, the condition being treated is decompression sickness and the gas comprises nitrogen. "Decompression sickness" means the disorder resulting from reduction of surrounding pressure (e.g., during ascent from a dive, exit from a caisson or hyperbaric chamber, or ascent to altitude), attributed to formation of bubbles from dissolved gas in blood or tissues, and usually characterized by pain and/or neurologic manifestations. The main inert gas for those who breathe air is nitrogen. The nitrogen bubbles result in the symptoms of decompression sickness which include itching skin, rashes, local joint pain, and neurological disturbance. In embodiments of a method of treating decompression sickness in a targeted region of the patient, a portion of the insonified perfluorocarbon droplet emulsions achieve formation of perfluorocarbon microbubbles. The perfluorocarbon microbubbles are undersaturated with dissolved gases, and thereby a concentration gradient favoring movement of the excess dissolved nitrogen gas molecules from the blood into the microbubbles is established for a time frame. The concentration differential results in the excess dissolved nitrogen gas molecules moving from the blood into the perfluorocarbon microbubble, thereby scavenging the excess dissolved nitrogen gas from the blood.

In other embodiments of a method of treating a patient for a condition characterized by an excess blood concentration of dissolved gas in at least one targeted region of the patient, the condition being treated is a pH-related biological condition and the gas comprises carbon dioxide. In some embodiments of a method of treating a patient for a condition characterized by an excess blood concentration of dissolved gas in at least one targeted region of the patient, the condition comprises acidosis. Acidosis can be caused by a buildup of carbon dioxide in the blood that results from poor lung function or depressed breathing. In embodiments of a method of treating a pH-related biological condition (including acidosis) in a targeted region of the patient, a portion of the insonified perfluorocarbon droplet emulsions achieve formation of perfluorocarbon microbubbles. The perfluorocarbon microbubbles are undersaturated with dissolved gases, and thereby a concentration gradient favoring movement of the excess dissolved carbon dioxide gas molecules from the blood into the microbubbles is established for a time frame. The concentration differential results in the excess dissolved carbon dioxide gas molecules moving from the blood into the perfluorocarbon microbubble, thereby scavenging the excess dissolved carbon dioxide gas from the blood.

In further embodiments of a method of treating a patient for a condition characterized by an excess blood concentration of dissolved gas in at least one targeted region of the patient, the condition being treated is selected from oxygen toxicity and reperfusion injury and the gas comprises oxygen. In embodiments of a method of treating oxygen toxicity or reperfusion injury in a targeted region of the patient, a portion of the insonified perfluorocarbon droplet emulsions achieve formation of perfluorocarbon microbubbles. The perfluorocarbon microbubbles are undersaturated with dissolved gases, and thereby a concentration gradient favoring movement of the excess dissolved oxygen gas molecules from the blood into the microbubbles is established for a time frame. The concentration differential results in the excess dissolved oxygen gas molecules moving from the blood into the perfluorocarbon microbubble, thereby scavenging the excess dissolved oxygen gas from the blood.

In some embodiments of a method of treating a patient for a condition characterized by an excess blood concentration of dissolved gas in at least one targeted region of the patient, the condition being treated is carbon monoxide poisoning and the gas comprises carbon monoxide. "Carbon monoxide poisoning" means the poisoning of a subject resulting from exposure to carbon monoxide. Toxicity of carbon monoxide can vary with the length of exposure, concentration of carbon monoxide that the subject was exposed to, respiratory and circulatory rates. Symptoms of carbon monoxide poisoning can vary with the percent carboxyhemoglobin present in the blood and can include headache, vertigo, dyspnea, confusion, dilated pupils, convulsions and coma (some of which result from injury to the brain). The standard treatment for carbon monoxide poisoning is the administration of 100% oxygen by breathing mask. In embodiments of a method of treating carbon monoxide in a targeted region of the patient, a portion of the insonified perfluorocarbon droplet emulsions achieve formation of perfluorocarbon microbubbles. The perfluorocarbon microbubbles are undersaturated with dissolved gases, and thereby a concentration gradient favoring movement of the excess dissolved carbon monoxide gas molecules from the blood into the microbubbles is established for a time frame. The concentration differential results in the excess dissolved carbon monoxide gas molecules moving from the blood into the perfluorocarbon microbubble, thereby scavenging the excess dissolved carbon monoxide gas from the blood.

In some embodiments of a method of treating a patient for a condition characterized by an excess blood concentration of dissolved gas in at least one targeted region of the patient, the method further comprises monitoring the treatment using imaging technology.

In some embodiments, the use of the perfluorocarbon droplet emulsions may be a component of a combination therapy or adjunct therapy. The combination therapy can be sequential or simultaneous. The perfluorocarbon droplet emulsions and other compounds can be administered independently by the same route or by two or more different routes of administration depending on the dosage forms employed. The dosage of the compounds administered in treatment will vary depending upon factors such as the pharmacodynamic characteristics of a specific therapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect. A dosage unit of the compounds may comprise a single compound or mixtures thereof with other compounds. The compounds can be introduced directly into the targeted tissue, using dosage forms well known to those of ordinary skill in the cosmetic and pharmaceutical arts.

For example, in some embodiments a method for releasing a pharmaceutical agent from a pH-sensitive delivery vehicle comprising the pharmaceutical agent to a target region of a patient is provided. In some embodiments, the method comprises administering the delivery vehicle comprising the pharmaceutical agent into the blood of the patient; administering a composition comprising a perfluorocarbon droplet emulsion into the blood of the patient; isonifying the target region sufficient to achieve formation of microbubbles by droplet vaporization of at least a portion of the perfluorocarbon droplets present in the blood; whereby a concentration gradient favoring movement of carbon dioxide molecules from the blood into the microbubbles is established for a time frame sufficient to reduce pH of the blood in the target region and cause release of the pharmaceutical agent from the delivery vehicle to the target region. The pH-sensitive delivery vehicle can be any pH-sensitive delivery vehicle as known in the art. A "pharmaceutical agent" means an active compound or compounds that are active pharmaceutical ingredients in a pharmaceutical formulation. "Active pharmaceutical ingredient" or "API" is defined by U.S. Food and Drug Administration as any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical and cosmetic practices. The compounds can be administered alone but are generally mixed with a pharmaceutically acceptable carrier. This carrier can be a solid or liquid, and the type of carrier is generally chosen based on the type of administration being used. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

EXAMPLES

The following examples are given by way of illustration and are in no way intended to limit the scope of the present invention.

Example 1

Materials and Methods 1.1 Preparation of Albumin-Coated Perfluoropentane (PFP) Droplets Albumin-coated PFP droplets were prepared based on a previously established protocol (see O. D. Kripfgans, J. B. Fowlkes, D. L. Miller, O. P. Eldevik, P. L. Carson, Acoustic droplet vaporization for therapeutic and diagnostic applications, Ultrasound Med. Biol. 26 (2000) 1177-1189, which is hereby incorporated by reference in its entirety). Briefly, 0.25 ml of dodecafluoropentane (Strem Chemicals, Newburyport, Mass., USA) was added gravimetrically to 2 ml vials followed by the addition of 0.75 ml of 4 mg/ml bovine serum albumin (Sigma Aldrich, St. Louis, Mo., USA) in phosphate buffered saline (PBS) (Sigma Aldrich). The vials were sealed with a rubber stopper, crimped, and placed on ice prior to amalgamation at 4800 rpm for 30 s in an amalgamator (WIG-L-BUG, Dentsply Rinn, Elgin, Ill., USA) at 5° C. to obtain albumin-coated PFP droplets. The vials were refrigerated for at least 24 h before use. Vials were used within 2 days of being manufactured. The size distribution of the droplets was measured with a Coulter counter (Multisizer 4, Beckman Coulter Inc., Brea, Calif., USA).

1.2 Experimental Setup

The albumin-coated PFP emulsion was diluted in air-saturated PBS (1:30 v/v) and slowly drawn into a 60 ml syringe through an 18 G needle. Using a syringe pump, the droplets in PBS were pumped through an in vitro flow phantom (FIG. 1) at 5 ml/min. The flow phantom consisted of polyvinyl chloride tubing (McMaster-Carr, Aurora, Ohio, USA), in-line dissolved oxygen (DO) sensors (OXFTC, Pyroscience, Aachen, Germany) and ethyl vinyl alcohol (EVA) tubing (McMaster) immersed in a tank of degas sed water maintained at 37° C. ADV was induced by a single-element 2 MHz focused transducer (H106, Sonic concepts, Bothell, Wash., USA) as the droplets flowed through the EVA tubing. Based on a previous study, the EVA tubing was used because it had an inner diameter of 1 mm which was comparable to the −6 dB elevational beamwidth of the 2 MHz focused transducer (1.1 mm), thin walls (0.38 mm), and high acoustic transmission coefficient (94%) to ensure uniform insonation of the droplets. The 2 MHz focused transducer had an aperture diameter of 6.3 cm and a focal distance of 6.4 cm.

B-mode images of the insonified droplets were acquired using an ultrasound research scanner (Vantage 1, Verasonics, Kirkland, Wash., USA) equipped with a linear array transducer (L7-4, center frequency 5 MHz, Philips, Bothell, Wash., USA), to monitor the formation of microbubbles. DO in the fluid was measured over 120 s using in-line DO sensors located upstream and downstream of the insonation region. Based on a flow rate of 5 mL/min, fluid took approximately 20 s to travel from the ultrasound focus to the downstream DO sensor. The in-line DO sensors consisted of a luer lock flow-through cell and a fiber optic spot fiber (SPFIB-Bare, Pyro Science GmbH, Aachen, Germany) connected to an optical oxygen meter (FireStingO2, Pyro Science). The DO sensors were calibrated according to the manufacturer's instructions to measure 100% DO in air-saturated PBS at 37° C. The effluent from the flow system was collected and diluted in PBS to obtain a final concentration of 1:8000 (v/v). The surviving droplets in the diluted effluent were measured in a Coulter counter (Multisizer 4, Beckman Coulter, Brea, Calif., USA) equipped with a 30 µm aperture.

1.3 Ultrasound Parameters

The acoustic output and the spatial beam profile of the 2 MHz transducer were calibrated up to 2 MPa peak rarefactional pressure using a 0.4 mm membrane hydrophone (Precision Acoustics, Dorchester, UK) mounted on a three-dimensional stepper-motor controlled system (Velmex NF90 Series, Velmex Inc., 291 Bloomfield, N.Y.). A linear relationship between the voltage applied to the transducer and the peak rarefactional pressures below 2 MPa was obtained. A linear extrapolation of this relationship was used to estimate peak rarefactional pressures above 2 MPa (see O. Bessonova, V. Wilkens, Membrane hydrophone measurement and numerical simulation of HIFU fields up to, IEEE Trans. Ultrason. Ferroelectr. Freq. Control. (2013), and J. A. Kopechek, E. Park, Y. Zhang, N. I. Vykhodtseva, N.J. McDannold, T. M. Porter, Cavitation-enhanced MR-guided focused ultrasound ablation of rabbit tumors in vivo using phase shift nanoemulsions, Phys. Med. Biol. 59 (2014) 3465, which are hereby incorporated by reference in its entirety). The −3 dB focal volume of the 2 MHz transducer was 0.7 mm×0.7 mm×5.4 mm (azimuth×elevation×range), thus allowing a relatively uniform pressure field inside the EVA tubing (inner diameter 1 mm).

Figure 2B:
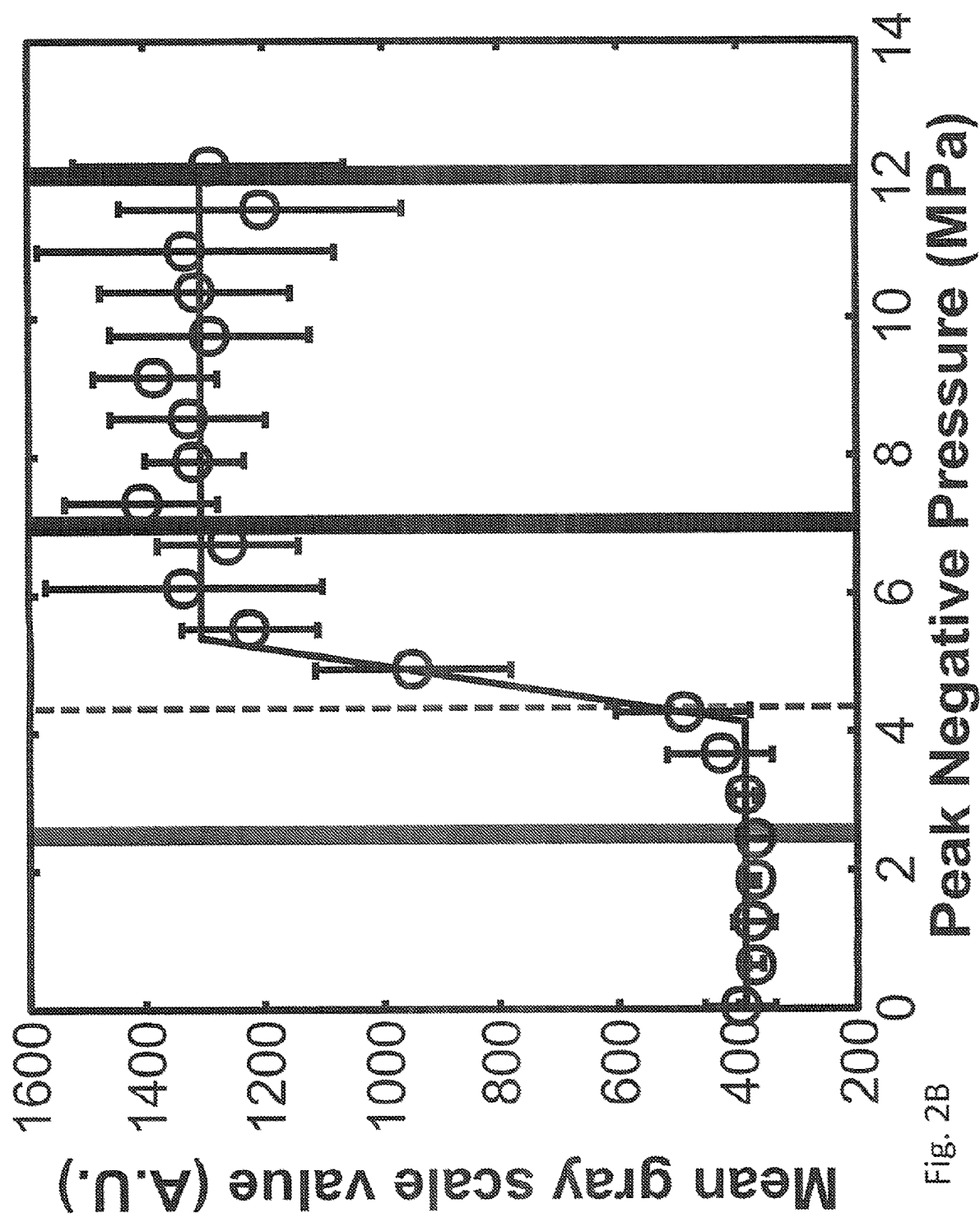
FIG. 2B shows a linear piece-wise function (black line) that was fit to the mean gray scale values. The ADV threshold was defined as the pressure where the first two lines of the piece-wise function intersected. The threshold pressure is indicated by the dotted line. The pressures indicated by the green, gray, and blue bars at 2.5 MPa, 7.3 MPa, and 12.2 MPa were used in subsequent experiments to measure changes in DO in the fluid induced by ADV.

The acoustic droplet vaporization threshold was determined using established methods based on changes in echogenicity (O.D. Kripfgans, J. B. Fowlkes, D. L. Miller, O. P. Eldevik, P. L. Carson, Acoustic droplet vaporization for therapeutic and diagnostic applications, Ultrasound Med. Biol. 26 (2000) 1177-1189) which is hereby incorporated by reference in its entirety). The peak rarefactional pressure of the 2 MHz transducer was ramped from 0 MPa to 12.2 MPa in steps of 0.6 MPa. The pulse repetition frequency was 100 Hz and the pulse duration was 5 µs. At each peak rarefactional pressure setting, a B-mode image of the droplets was acquired. The mean grayscale value was ascertained within a region of interest defined in the lumen downstream of the 2 MHz insonation location (FIG. 2A). A piece-wise linear fit of the mean grayscale value as a function of the peak rarefactional pressure was used to define the acoustic droplet vaporization threshold. The threshold was defined as the rarefactional pressure amplitude corresponding to the intersection between the first two lines of the piece-wise linear fit based on previous studies (FIG. 2B). The threshold was determined for four vials of the PFP droplets (one measurement per vial) and the mean and standard deviation of the thresholds were computed after confirming the normality of the data using the Jarque Bera test in MATLAB® (Mathworks, Natick, Mass., USA). Based on this ADV threshold, the PFP droplets were subsequently insonified at peak rarefactional pressures greater than and less than the ADV threshold to quantify changes in DO in the fluid.

1.4 Mathematical Model

Prior to exposure to ultrasound, the fluid system consisted of two components, namely the PFP droplets and the surrounding PBS liquid. Upon exposure to ultrasound a fraction of the droplets underwent ADV and were converted into microbubbles. Therefore the fluid system after ultrasound exposure consisted of three components, PFP microbubbles, the surviving PFP droplets, and the surrounding fluid (PBS). At equilibrium, the partial pressure of oxygen in the PFP microbubbles, the surviving PFP droplets, and the surrounding PBS liquid are equal as shown in equation 1.

$$\frac{RTn_b}{V_b} = \frac{kn_d}{SV_d} = \frac{kn_l}{V_l}, \qquad (1)$$

where the first term is the partial pressure of oxygen in the PFP microbubbles given by the ideal gas law, R is the ideal gas constant, T is the temperature, $V_b$ is the total volume of the PFP microbubbles, and $n_b$ is the number of moles of oxygen in the microbubbles. The second term is the partial pressure of oxygen in the droplet according to Henry's law, where S is the ratio of solubility of oxygen in liquid PFP (80% v/v) to that in water (3% v/v), k is Henry's constant for oxygen in water (759 L·atm/mol), $n_d$ is the number of moles of oxygen in the droplets surviving ultrasound exposure, and $V_d$ is the total volume of the PFP liquid droplets surviving ultrasound exposure. The third term is the partial pressure of oxygen in the surrounding liquid using Henry's law where $n_l$ is the number of moles of oxygen in the surrounding liquid, and $V_l$ is the volume of the surrounding liquid.

Further, based on the law of conservation of mass in a closed system, the total number of moles of oxygen in the fluid system should remain constant before and after ultrasound exposure as shown in equation 2.

$$\frac{P_{d0}V_{d0}S + P_{l0}V_l}{k} = n_b + n_d + n_l \qquad (2)$$

The left hand side of the equation is the number of moles of oxygen in the fluid system before ultrasound exposure and the right hand side of the equation is the number of moles of oxygen in the fluid system after ultrasound exposure. $P_{l0}$ is the initial partial pressure of oxygen in the liquid surrounding the droplets which is measured by the upstream DO sensor. $P_{d0}$ is the initial partial pressure of oxygen in the PFP droplets without ultrasound exposure and is assumed to be in equilibrium with $P_{l0}$. $V_{d0}$ is the total volume of all of the PFP droplets in the effluent without being exposed to ultrasound.

The total volume of droplets in the effluent before exposure to ultrasound ($V_{d0}$), as well as the total volume of droplets in the effluent after ultrasound exposure ($V_d$), were measured using a Coulter counter 10 min after collecting a sample of the effluent. The sample was allowed to sit 10 min at room temperature to allow any microbubbles to either dissolve or float out of solution. To assess whether any microbubbles were present in the sample after 10 min, the acoustic attenuation spectra of the sample containing droplets with and without ultrasound exposure were measured from two vials of droplets (see J. L. Raymond, K. J. Haworth, K. B. Bader, K. Radhakrishnan, J. K. Griffin, S. Huang, D. D. McPherson, C. K. Holland, Broadband attenuation measurements of phospholipid-shelled ultrasound contrast agents, Ultrasound Med. Biol. 40 (2014) 410-421, which is hereby incorporated by reference in its entirety). A Kolmogorov-Smirnov test resulted in a p-value greater than 0.05, indicating that the attenuation spectra of the droplets with and without ultrasound exposure were not significantly different. From this it was inferred that the effluent only contained droplets.

The fraction of surviving droplets at each diameter was defined as the ratio of the number density of droplets after ultrasound exposure to the number density of droplets without ultrasound exposure. Based on calculations made by Kripfgans et al., the microbubbles formed upon ADV undergo a volumetric expansion by a factor of 125 at 37° C. Additionally, as reported in several studies, the microbubble grows due to ingassing. At equilibrium, the microbubble volume based on the ideal gas law will be:

$$V_b = \frac{RT}{P_{atmosphere}}(n_{PFP} + n_{O_2} + n_{N_2} + n_{Ar} + n_{CO_2} + n_{Ne} + n_{He}), \quad (3)$$

where n denotes the number of moles of gas and the subscripts denote the different gases that will be present in the microbubble after ingassing. The proportions of each non-PFP gas in the microbubble will be the same as the proportions of each non-PFP gas dissolved in the fluid, which in turn was equilibrated with air. Therefore the proportions of each non-PFP gas in the microbubble will be the same as the proportions of the gases in standard air nitrogen composing approximately 78%, oxygen composing approximately 21%, et cetera). Equation 3 can be rewritten as:

$$V_b = \frac{RTn_{PFP}}{P_{atmosphere}} + \frac{RT}{P_{atmosphere}} \cdot \left(n_{O_2} \cdot \frac{n_{air}}{n_{O_2}}\right), \quad (4)$$

where $n_{air}$ is the number of gas molecules that compose a unit volume of standard air. The total number of air molecules to oxygen molecules is 4.7733. Further, $n_{O_2}$ in equation 4 is equal to $n_b$ as defined in equation 2. The total volume of the microbubbles ($V_b$) can therefore be rewritten by expressing the first term in equation 4 in terms of the total volume of droplets that were vaporized during ADV and the expansion factor of 125, as:

$$V_b = (V_{d0} - V_d) \times 125 + \frac{4.7733 \cdot n_b RT}{P_{atmosphere}} \quad (5)$$

By solving equations 1, 2, and 5, simultaneously, the number of moles of oxygen in the liquid per unit volume $n_l/V_l$ can be calculated. The percent dissolved oxygen in the surrounding fluid after ultrasound exposure is predicted to be:

$$DO_l = \frac{kn_l}{V_l P_{l0}} \times DO_{l0}, \quad (6)$$

where $DO_{l0}$ is the initial dissolved oxygen in the liquid surrounding the PFP droplets and $DO_l$ is the predicted dissolved oxygen in the surrounding liquid in equilibrium with phase-transitioned PFP droplets after ultrasound exposure.

1.5 Centrifugation of Droplets

Transitioning droplets in the arterial system after intravenous injection requires the droplets to flow through the pulmonary capillaries. Previous studies estimated the size distribution of ultrasound contrast agents that pass through the lungs based on the size distribution of the pulmonary capillaries (see N. d. Jong, F. Ten Cate, W. Vletter, J. Roelandt, Quantification of transpulmonary echocontrast effects, Ultrasound Med. Biol. 19 (1993) 279-288 and J. C. Hogg, Neutrophil kinetics and lung injury, Physiol. Rev. 67 (1987) 1249-1295, hereby incorporated by reference in their entirety). The same technique was applied to estimate the size distribution of droplets that would pass through the lung. Briefly, the size distribution of human lung capillaries was used to compute a cumulative probability density function for passage of particles through the pulmonary capillary bed. It was assumed that each droplet was likely to pass through the lungs if it had a smaller diameter than the pulmonary capillary. The cumulative probability density function was multiplied by the number density size distribution of the droplets.

The size distribution of the droplets was subsequently modified using centrifugation to remove a large fraction of the droplets that would not be predicted to survive lung filtration. Centrifugation techniques have been previously used for size separation of ultrasound contrast agent microbubbles. The PFP emulsion was diluted in PBS (1:4.8 v/v) and centrifuged at a relative centrifugal force of 9 g for 5 min at 21° C. (Allegra, Beckman Coulter). After centrifugation, 2.88 ml of the supernatant was collected. The centrifugation speed and time were selected so that only droplets that were approximately 6 μm or less remained in the supernatant. These droplets, which will be referred to as centrifuged droplets, were used in the subsequent ultrasound experiments.

1.6 Computed Droplet Size Distributions and Concentrations

In order to determine an optimal droplet size distribution and concentration for in vivo applications, the trade-off between maximum gas scavenging and the potential for droplets to occlude lung capillaries after intravenous injection were considered. Larger droplets undergo a phase-transition more efficiently, but also have a higher probability of occluding pulmonary capillaries. Another limitation is the maximum concentration of droplets within the blood stream that can be tolerated by the body. Previous studies of perfluoropentane droplets in animals (rabbits and canines) have not reported adverse events when the estimated in vivo concentrations are approximately $10^5$ to $10^6$ droplets/ml. This concentration range is similar to the FDA approved concentration of perfluorocarbon-based ultrasound contrast agents in humans, based on the calculation of a bolus injection diluted by the total blood volume in humans ($5 \times 10^6$ microbubbles/ml).

A set of computations were performed to determine a size distribution of PFP droplets with an in situ concentration of no more than $5 \times 10^6$ droplets/ml that would cause at least a 50% decrease in DO in the fluid surrounding the droplets. Gaussian probability density functions with a range of standard deviations from 0.1 μm to 4 μm in steps of 0.1 μm were used to represent size-isolation filters. Experimentally obtained size distributions of centrifuged droplets without and with ultrasound exposure were multiplied by these size isolation filters to obtain a family of curves that represented computationally modified size distributions. The computed droplet-size distribution with the smallest mean diameter that was predicted to lower the DO in the fluid to 50% at a concentration of $5 \times 10^6$ droplets/ml was selected. This computationally modified size distribution was subsequently scaled to vary the concentration of droplets from $10^3$ to $10^9$ droplets/ml. The predicted dissolved oxygen concentration in the fluid surrounding the computationally modified size distributions were calculated as described in section 2.4.

1.7 Statistical Analysis

Measured and predicted DO values were compared using the Student's t-test in QuickCalcs (GraphPad, La Jolla, Calif., USA). Differences in volume-weighted number density size distributions were assessed using the Kolmogorov-Smirnov test in MATLAB®. For all statistical tests, a p-values less than 0.05 used to denote a statistically different result.

Example 2

Results and Discussion

2.1 Ultrasound-Mediated Phase-Transition Response

Figure 3A:
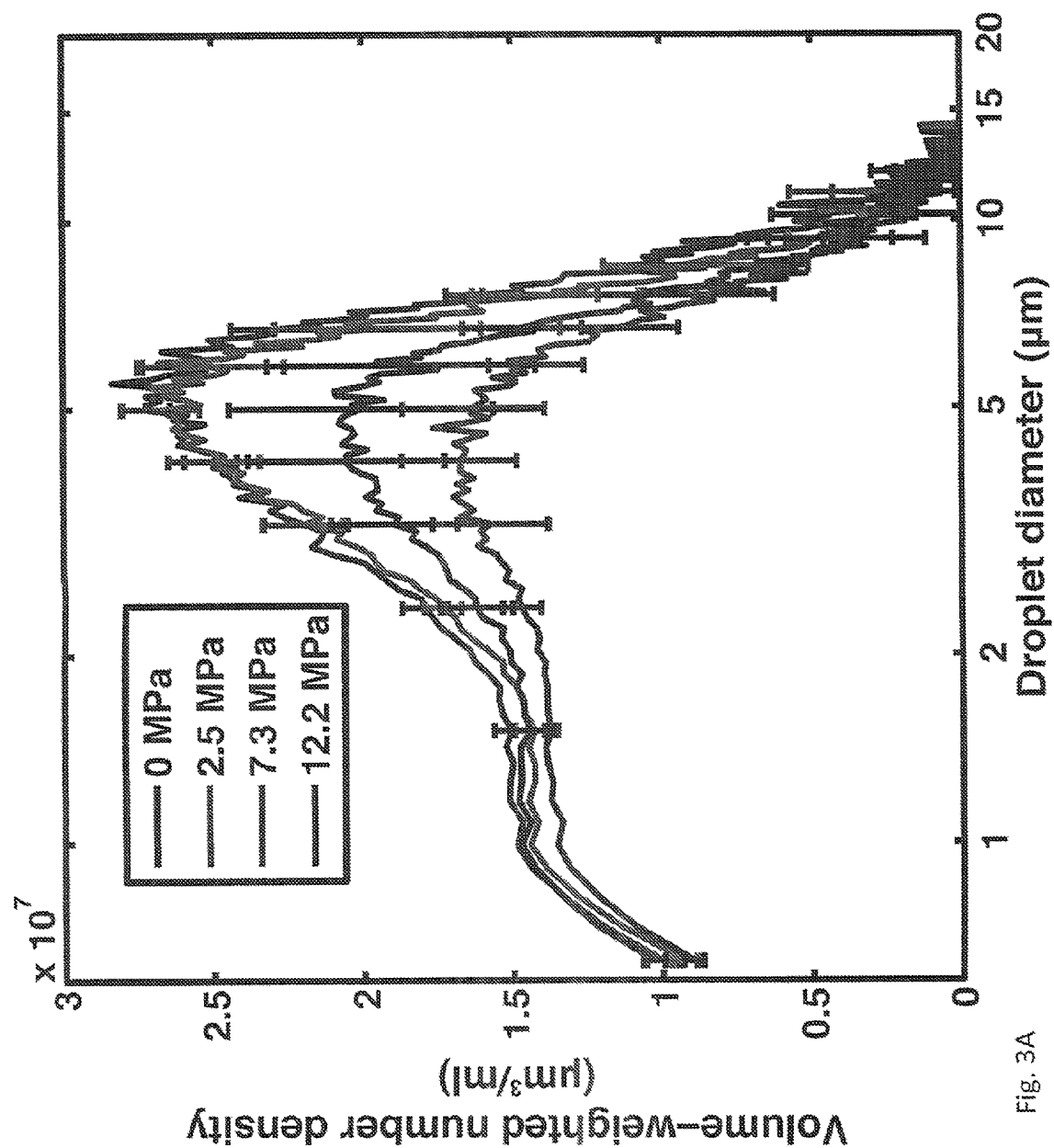
FIG. 3A shows the volume-weighted number-density size distribution of non-centrifuged PFP droplets in the effluent without ultrasound exposure (0 MPa) and after ultrasound exposure at 2.5 MPa, 7.3 MPa, and 12.2 MPa (peak rarefactional). Error bars indicate the standard deviation of three measurements.
Figure 3B:
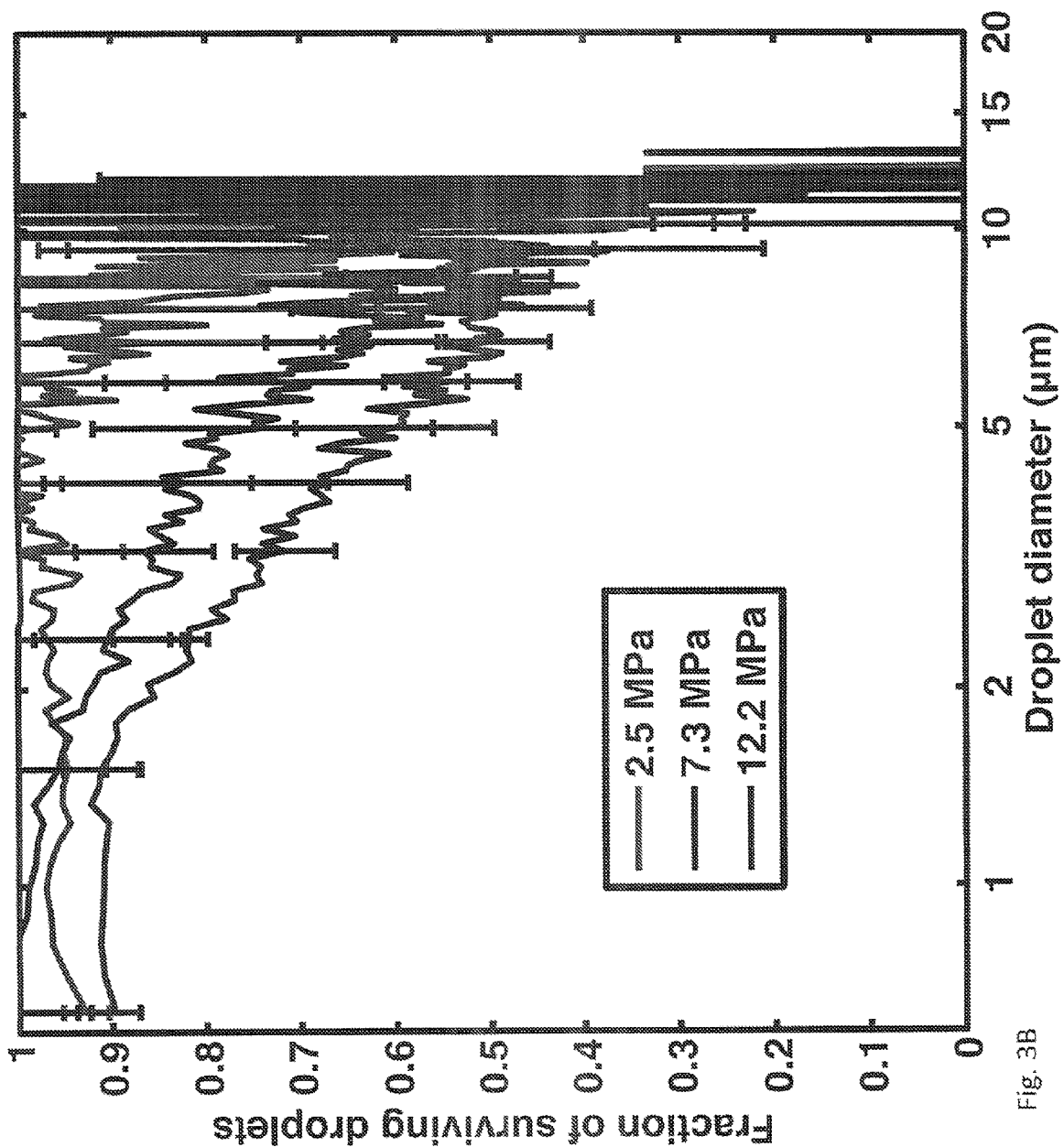
FIG. 3B shows the fraction of surviving PFP droplets calculated as the ratio of number of droplets surviving ultrasound exposure (2.5 MPa, 7.3 MPa, and 12.2 MPa) to the number of droplets measured without ultrasound exposure (0 MPa). Error bars indicate the propagated error based on the standard deviations from FIG. 3A.

FIG. 2b shows that the ADV threshold of non-centrifuged PFP droplets insonified by pulses with a 2 MHz center frequency, 5 μs pulse duration, and 100 Hz PRF was 4.2±0.7 MPa (peak rarefactional). It was noted that at larger insonation pressure amplitudes, the B-mode image was saturated and shadowing was observed due to the higher concentration of ADV-induced PFP microbubbles in the downstream ROI. Based on the ADV threshold, subsequent insonations of the droplets were carried out at peak rarefactional pressures of 2.5 MPa, 7.3 MPa, and 12.2 MPa. The volume-weighted number-density size distribution of PFP droplets without ultrasound exposure and with ultrasound exposure are shown in FIG. 3a. FIG. 3b shows the surviving fraction of droplets after ultrasound exposure (i.e. the ratio of the number of surviving PFP droplets to the number of PFP droplets in the effluent with no ultrasound exposure). Droplets smaller than 2 μm did not transition appreciably using this particular ultrasound exposure scheme. Above 2 μm, the fraction of surviving droplets decreased approximately linearly.

The net radial expansion of the droplets into microbubbles due to ADV and subsequent ingassing was calculated for the total volume of microbubbles using equation 7 to provide an average expansion across all droplet sizes:

$$\text{radial expansion} = \left(\frac{V_b}{V_{d0} - V_d}\right)^{1/3}. \tag{7}$$

The radial expansion factor was 6.8, 5.6, and 5.4 for droplets exposed to 2.5 MPa, 7.3 MPa, and 12.2 MPa respectively.

The ADV pressure threshold ascertained in the current study was 4.2±0.7 MPa (peak rarefactional) using pulses with a center frequency of 2 MHz, a pulse duration of 5 μs, and a PRF of 100 Hz (FIG. 2B). An ADV threshold of 3.1 MPa peak rarefactional pressure is predicted at 2 MHz using the inverse square relationship between insonation frequency and ADV thresholds ascertained by Kripfgans et al. The higher ADV threshold measured using our system could be due to the difference in transducer geometries, focal volume sizes, and consequent nonlinear propagation, as well as the amount of albumin used to make the droplets.

The surviving fraction of droplets after ultrasound exposure shown in FIG. 3B can be used to calculate the ADV efficiency as defined by Fabiilli et al., which is the fraction of droplets that vaporize (see M. L. Fabiilli, K. J. Haworth, I. E. Sebastian, O.D. Kripfgans, P. L. Carson, J. B. Fowlkes, Delivery of chlorambucil using an acoustically-triggered perfluoropentane emulsion, Ultrasound Med. Biol. 36 (2010) 1364-1375, which is hereby incorporated by reference in its entirety). The relationship between the surviving fraction of droplets after ultrasound exposure and the droplet diameter (FIG. 3B) was qualitatively similar to observations on transition efficiency made by Fabiilli et al., who used a 6.3 MHz insonation. Fabiilli et al. also observed that droplets smaller than 2 μm did not transition efficiently and the ADV efficiency increased linearly with droplet diameters between 2 μm and 12 μm. The reduced transition efficiency below 2 μm is also consistent with the superharmonic focusing theory of ADV that was proposed by Shpak et al. (see. O. Shpak, M. Verweij, H. J. Vos, N. de Jong, D. Lohse, M. Versluis, Acoustic droplet vaporization is initiated by superharmonic focusing, Proc. Natl. Acad. Sci. U.S.A 111 (2014) 1697-1702, which is hereby incorporated by reference in its entirety). Shpak et al. demonstrated that the spherical shape of the droplet and the acoustic impedance mismatch between the perfluorocarbon and the surrounding medium resulted in the focusing of superharmonics inside the droplet causing a gain in the rarefactional pressure amplitude. Based on this study, as the droplet diameter decreases the focal gain also decreases. Therefore it is less likely that a small droplet will phase transition during ultrasound insonation.

For insonation pressures above the ADV pressure threshold, the net radial expansion factor was 5.6 and 5.4 for 7.3 MPa and 12.2 MPa insonations, respectively. This radial expansion is slightly greater than the radial expansion predicted by the ideal gas law (5.0×), similar to the experimentally measured radial expansion reported by Kripfgans et al. (5.3×) and smaller than the expansion measured by Sheeran et al. (10×) (see P. S. Sheeran, V. P. Wong, S. Luois, R. J. McFarland, W. D. Ross, S. Feingold, T. O. Matsunaga, P. A. Dayton, Decafluorobutane as a phase-change contrast agent for low-energy extravascular ultrasonic imaging, Ultrasound Med. Biol. 37 (2011) 1518-1530) and Reznik et al. (50×) (see N. Reznik, M. Seo, R. Williams, E. Bolewska-Pedyczak, M. Lee, N. Matsuura, J. Gariepy, F. S. Foster, P. N. Burns, Optical studies of vaporization and stability of fluorescently labelled perfluorocarbon droplets, Phys. Med. Biol. 57 (2012) 7205). Based on the model developed in this study, the amount of ingassing depends on the concentration of microbubbles formed as well as the concentration of dissolved gases in the vicinity of these bubbles. For very dilute suspensions of microbubbles, more gas will flow into the microbubbles to reach equilibrium. For more concentrated suspensions less gas will flow into each microbubble to reach equilibrium in a closed system. It is possible that differences in droplet concentration between Kripfgans et al., Sheeran et al., Reznik et al., and the current study could explain the differences in observed radial expansion. The observed trend of a lower radial expansion for higher insonation pressures, which corresponded with more droplets converted into microbubbles per unit volume, is consistent with this hypothesis.

Figure 4:
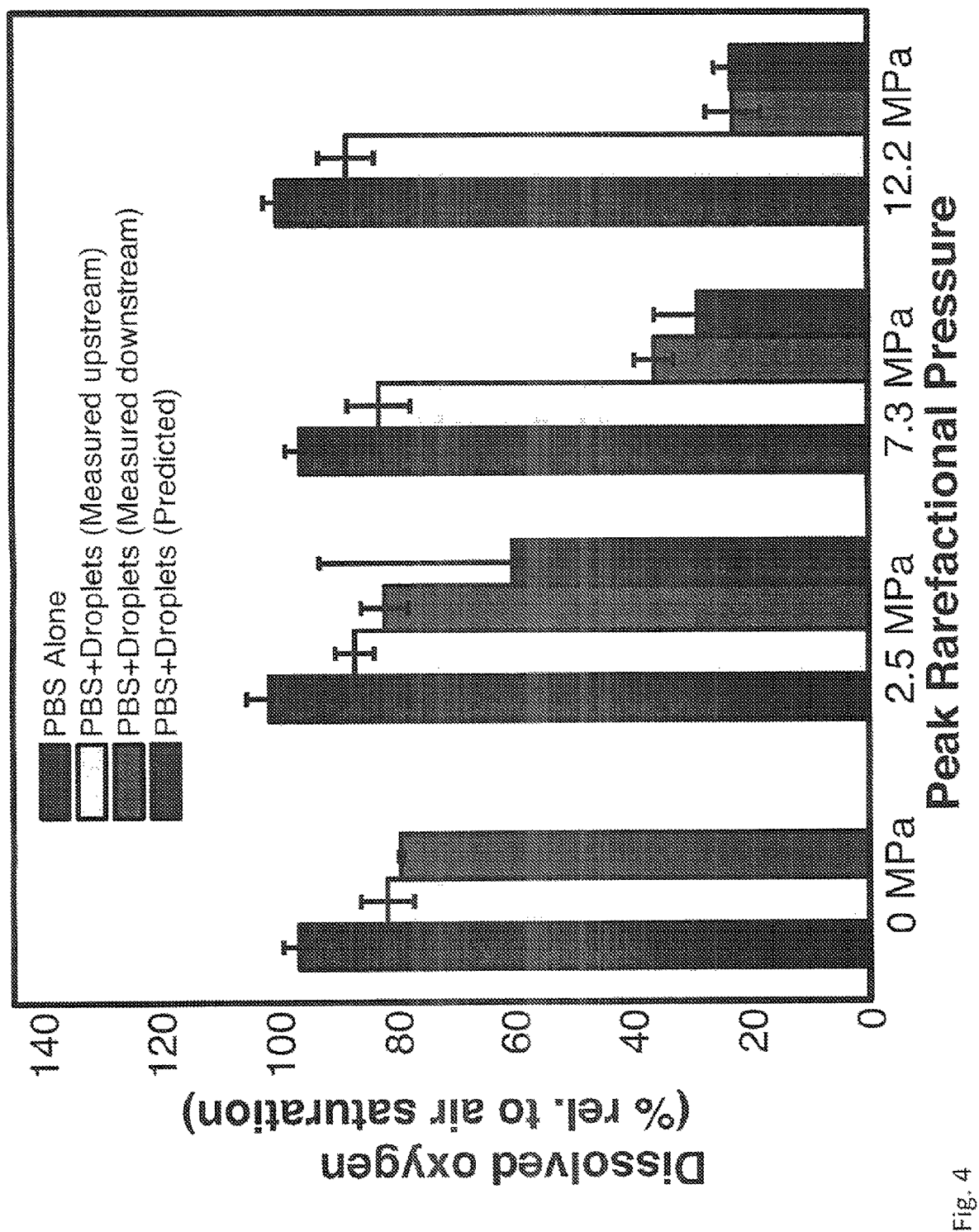
FIG. 4. Dissolved oxygen of fluids exposed to different insonation pressures.

2.2 Effect of Acoustic Peak Rarefactional Pressure on DO in Fluid Containing PFP Droplets The non-centrifuged droplets were insonified by peak rarefactional pressure amplitudes lower than (2.5 MPa) and greater than (7.3 MPa and 12.2 MPa) the ADV threshold pressure amplitude (4.2±0.7 MPa) to ascertain changes in dissolved oxygen in the surrounding fluid due to ADV. FIG. 4 shows the DO measured for air-saturated PBS alone (average value from both sensors), for the PBS surrounding the droplets as a function of insonation pressure, and the numerically predicted DO. The DO of the air-saturated PBS alone was 97±3% both upstream and downstream of the insonation region. The addition of PFP droplets resulted in a decrease in the DO to 84±3% without ultrasound exposure (0 MPa).

The DO in the surrounding fluid after insonifying the PFP droplets with ultrasound at 2.5 MPa peak rarefactional pressure was not statistically significantly different from the DO of the fluid surrounding the droplets upstream of the 2.5 MPa ultrasound insonation. The downstream DO measurement at 2.5 MPa was also not statistically significantly different from the DO with no ultrasound exposure (0 MPa) (FIG. 4). At acoustic pressure amplitudes exceeding the ADV threshold, the downstream DO in the surrounding fluid decreased to 36±3% and 27±5% after ultrasound exposure at 7.3 MPa and 12.2 MPa, respectively (FIG. 4). The predicted DO values were not statistically different from the measured downstream values of the DO.

FIG. 4 shows that the DO of the PBS alone was 97±3% and that the addition of non-centrifuged droplets with no ultrasound exposure (0 MPa peak rarefactional pressure amplitude) caused the DO to drop to 84±3% at 37° C. The DO of the fluid surrounding the non-centrifuged droplets measured at the outlet of the infusion syringe was 90±1%. It was also noted that spontaneous vaporization of PFP droplets occurred on the surface of the syringe plunger. These bubbles from spontaneous vaporization also scavenged oxygen resulting in a drop in the DO from 97±3% to 90±1%. The DO in the fluid surrounding the non-centrifuged droplets with the upstream and downstream sensors was 91±1% at 22° C. Few if any microbubbles from spontaneous vaporization were visually observed in the flow phantom at 22° C. However, when the droplets were injected, gas bubbles from spontaneous vaporization were observed in the flow system at 37° C. Thus spontaneous vaporization in the tubing also accounts for the DO drop from 90±1% to 84±3%. Furthermore, spontaneous vaporization would be expected to occur more readily as the droplet diameter increases due to a lower Laplace pressure. This assumption is consistent with the observation that the DO in the fluid surrounding centrifuged droplets at 37° C. was higher (93±3%) than non-centrifuged droplets (84±3%), even though the number densities of centrifuged and non-centrifuged droplets were similar.

FIG. 4 also shows that the DO in the fluid decreased with increasing insonation pressure. This observation is likely due to a larger fraction of droplets undergoing ADV (FIG. 3) resulting in a greater amount of oxygen being scavenged after a 12.2 MPa insonation compared to a 7.3 MPa insonation. This explanation is supported by the numerical predictions. No statistically significant differences were observed between the measured and predicted DO in the fluid after ADV. The peak rarefactional pressure amplitude exposure dictates the fraction of droplets transitioned into PFP microbubbles and therefore also dictates the amount of DO scavenged from the surrounding fluid based on conservation of mass and equal partial pressures at equilibrium.

Note that the mathematical model is simplistic and accounts for the DO in the fluid at equilibrium, neglecting microbubble dissolution. This model does not take into consideration the temporal kinetics of diffusion of gases into and out of the PFP microbubbles. We note that Kripfgans et al. predicted that ingassing would occur within hundreds of milliseconds, which is consistent with the experimentally measured growth of microbubbles reported by Kang et al. (see S. Kang, Y. Huang, C. Yeh, Characterization of acoustic droplet vaporization for control of bubble generation under flow conditions, Ultrasound Med. Biol. 40 (2014) 551-561). The microbubbles (including perfluoropentane, nitrogen, oxygen, etc.) would subsequently dissolve over tens of seconds. Kripfgans et al. predicted that the microbubble diameter would be within 90% of its maximum diameter 20 s after ultrasound exposure. Our dissolved oxygen measurements were made within 20 s of ultrasound exposure, likely before significant dissolution occurred.

The numerical model also does not account for changes in the microbubbles due to continued acoustic insonation. Based on the volumetric flow rate and pulse repetition frequency used in this study, it was estimated that the droplets would be exposed to 7-8 ultrasound pulses, each approximately 10 cycles in duration, in the focal volume. Previous studies have described the effects of rectified diffusion and acoustically driven diffusion on the gas content within a microbubble. These phenomena could increase or decrease the dissolved oxygen in the fluid. Fragmentation of the microbubbles may also occur at these insonation pressures. However as long as the PFP gas does not dissolve rapidly, the total volume of PFP gas available to scavenge dissolved oxygen does not change and therefore the total volume of scavenged oxygen would not change. Future revisions to the model can be developed to incorporate these microbubble dynamics.

An additional limitation of the model is that it does not take into account surface tension, which could cause size dependent effects on the expansion. However, Sheeran et al. showed that the expansion factor does not depend on droplet diameter for droplets greater than approximately 3 μm in diameter. In this study and the study by Fabiilli et al., few droplets less than 3 μm in diameter were phase-transitioned, which, as described above, is consistent with the superharmonic focusing theory of acoustic droplet vaporization. Therefore the effects of surface tension were not included in the model. However other studies have used nanodroplets to nucleate ADV. In order to provide an accurate estimate of the amount of dissolved oxygen scavenged by bubbles produced from nanodroplets, the radius-dependent Laplace pressure must be considered. The inclusion of the Laplace pressure in the model would likely result in a decreased amount of dissolved oxygen being scavenged.

Despite these limitations, the DO predictions from the mathematical model agreed with the measured values (p-values were equal to 0.32, 0.18, and 0.95 for 2.5 MPa, 7.3 MPa, and 12.2 MPa insonations, respectively).

The numerical model and experiments were limited to scavenging dissolved oxygen, which may have applications in treating reperfusion injury. Further, the effect should be applicable to other dissolved gases because the mechanism is based on diffusion gradients. This effect might have potential use in scavenging carbon dioxide and nitrogen for treating localized acidosis and decompression sickness, respectively. The effect has already been explored using spontaneous vaporization (i.e. no ultrasound) of a perfluoropentane emulsion for nitrogen scavenging.

2.3 Effect of Size Distribution of Droplets on DO in Fluid

Figure 5A:
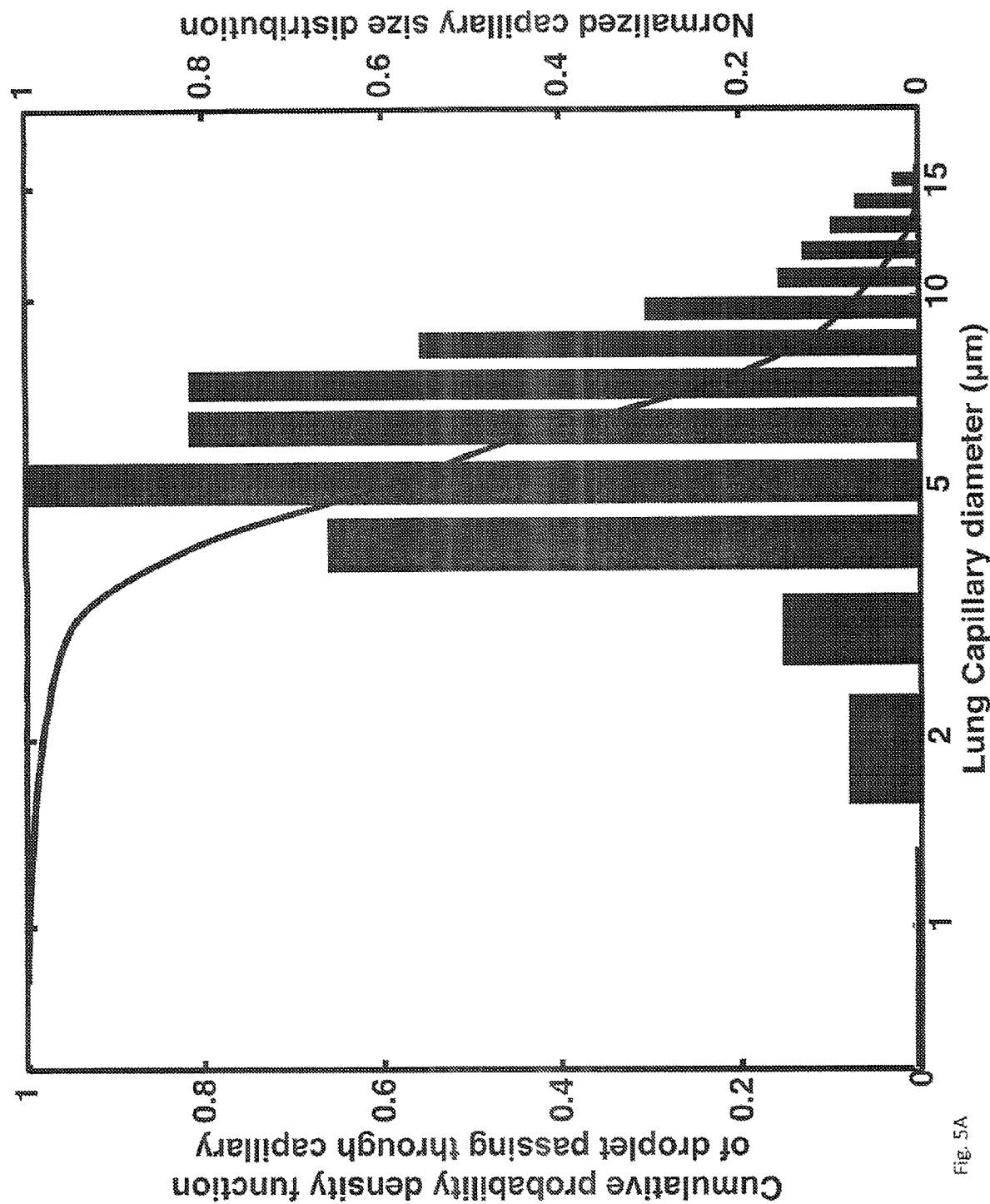
FIG. 5A shows the number density of capillaries in human lung (Hogg et al 1987) is shown as a bar plot and cumulative probability density function of a droplet passing through lung capillaries shown as a black curve.
Figure 5B:
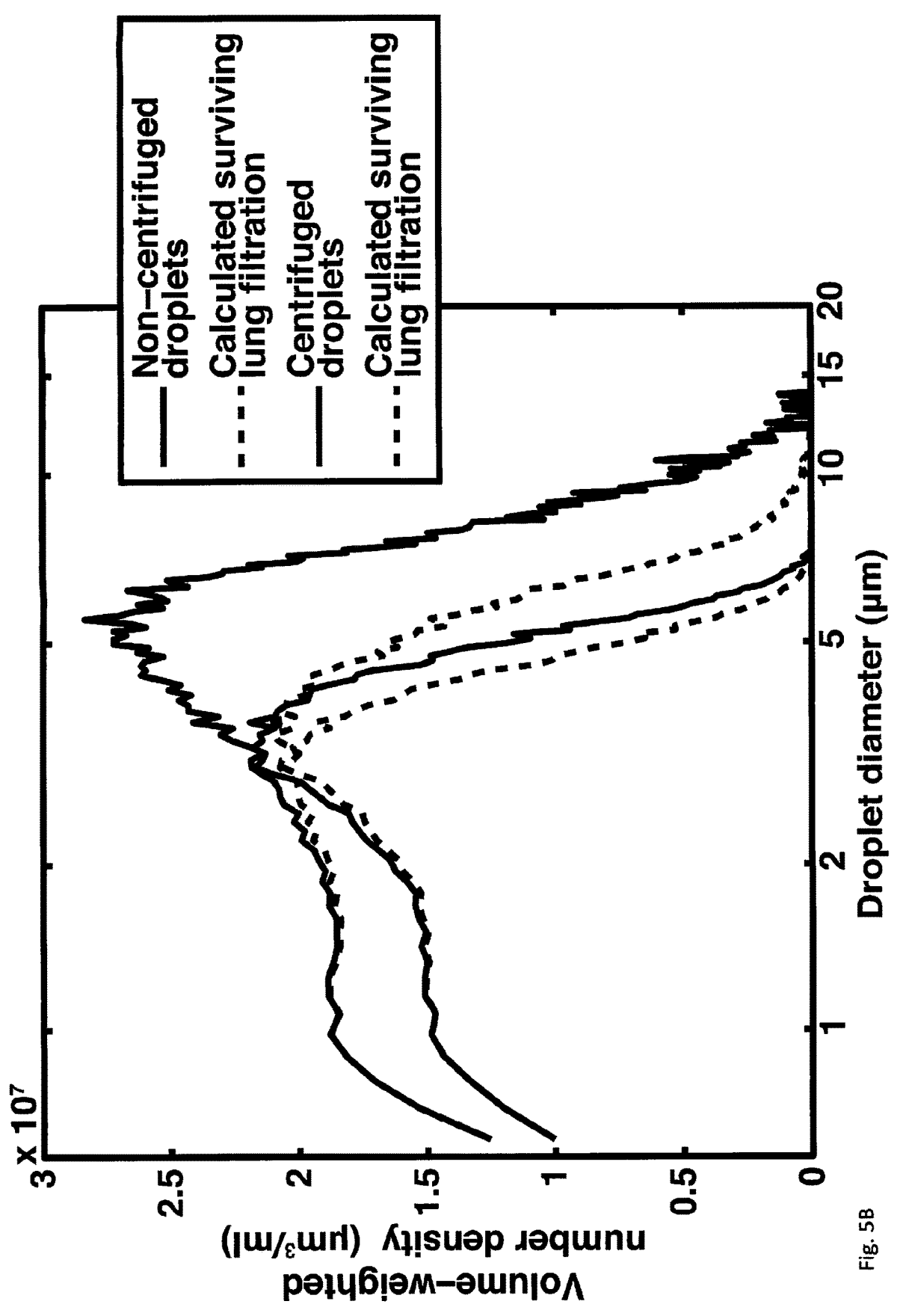
Figure 6A:
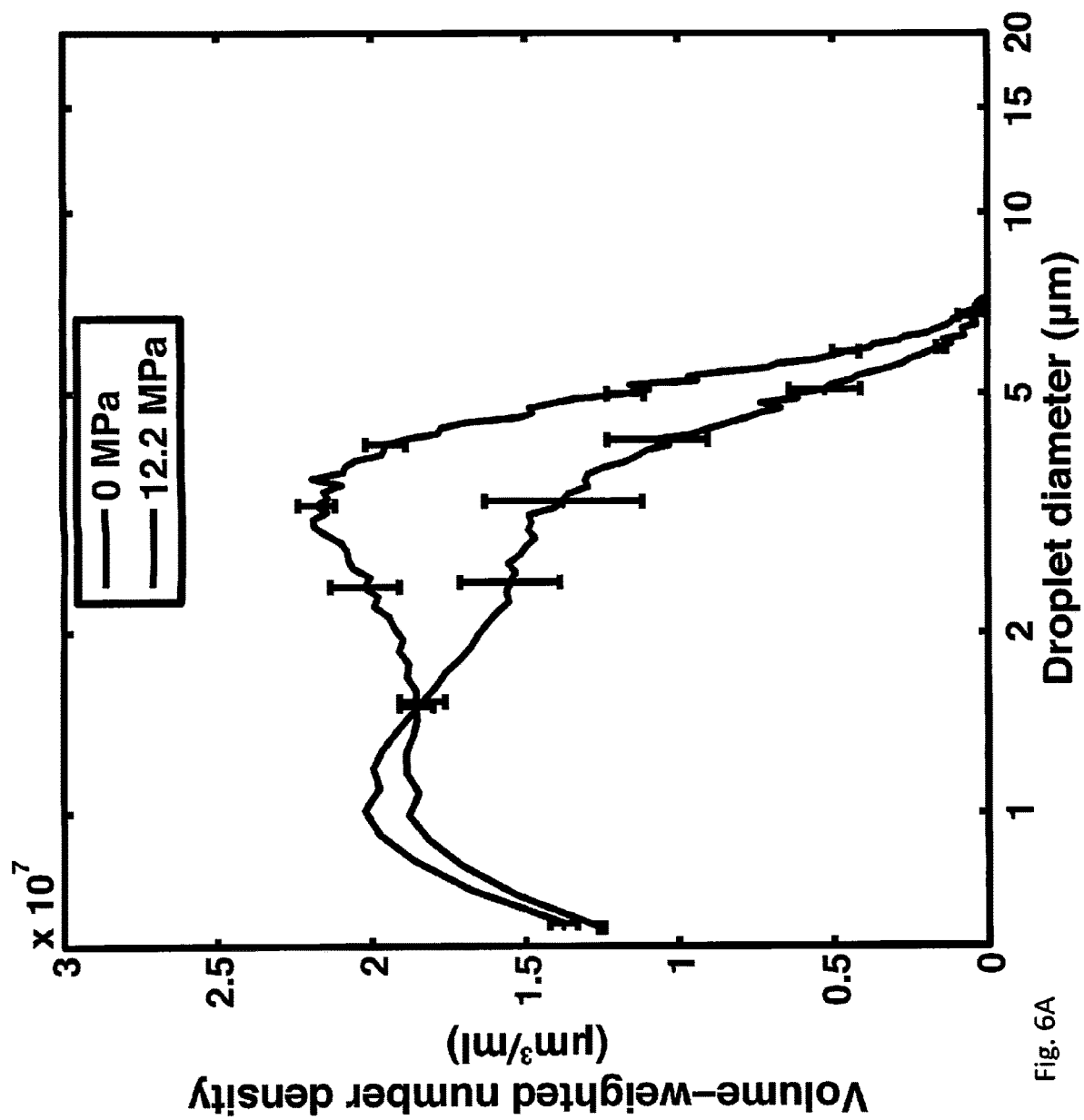
FIG. 6A shows measured volume-weighted number-density size distribution of centrifuged PFP droplets in flow alone and after 12.2 MPa peak rarefactional ultrasound exposure. Error bars indicate the standard deviation of three measurements.
Figure 6B:
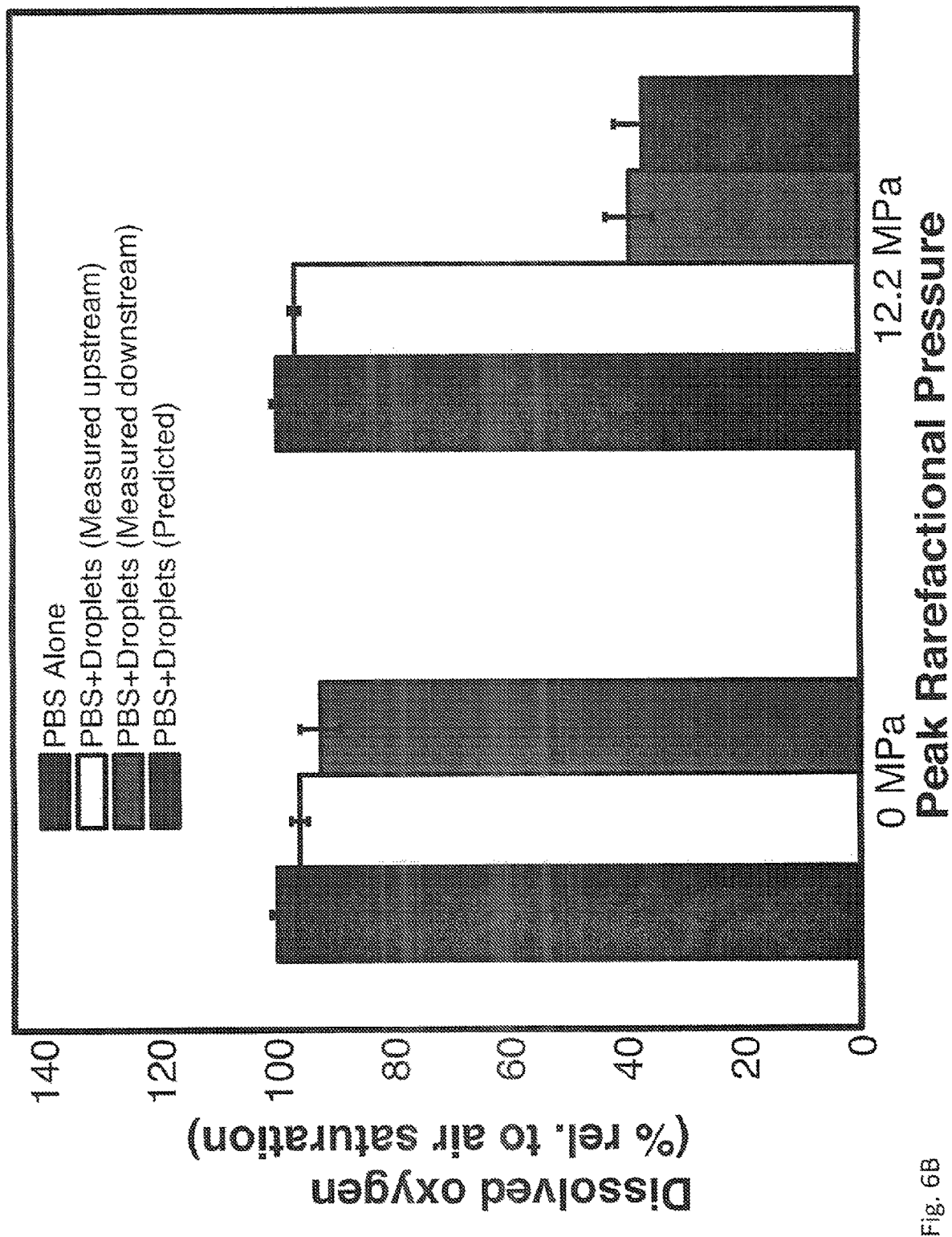
FIG. 6B shows percent dissolved oxygen measured with air-saturated PBS alone (black bars), measured upstream of the insonation region with centrifuged droplets (tan bars), and measured downstream of the insonation region with centrifuged droplets (orange bars) in the absence (0 MPa) and presence (12.2 MPa) of ultrasound exposure. Error bars indicate the standard deviation of three measurements. The predicted dissolved oxygen (violet bar) was not statistically different than the dissolved oxygen measured downstream of the insonation region. Error bars indicate the propagated error based on the standard deviations from FIG. 6A and equation 6.
Figure 7A:
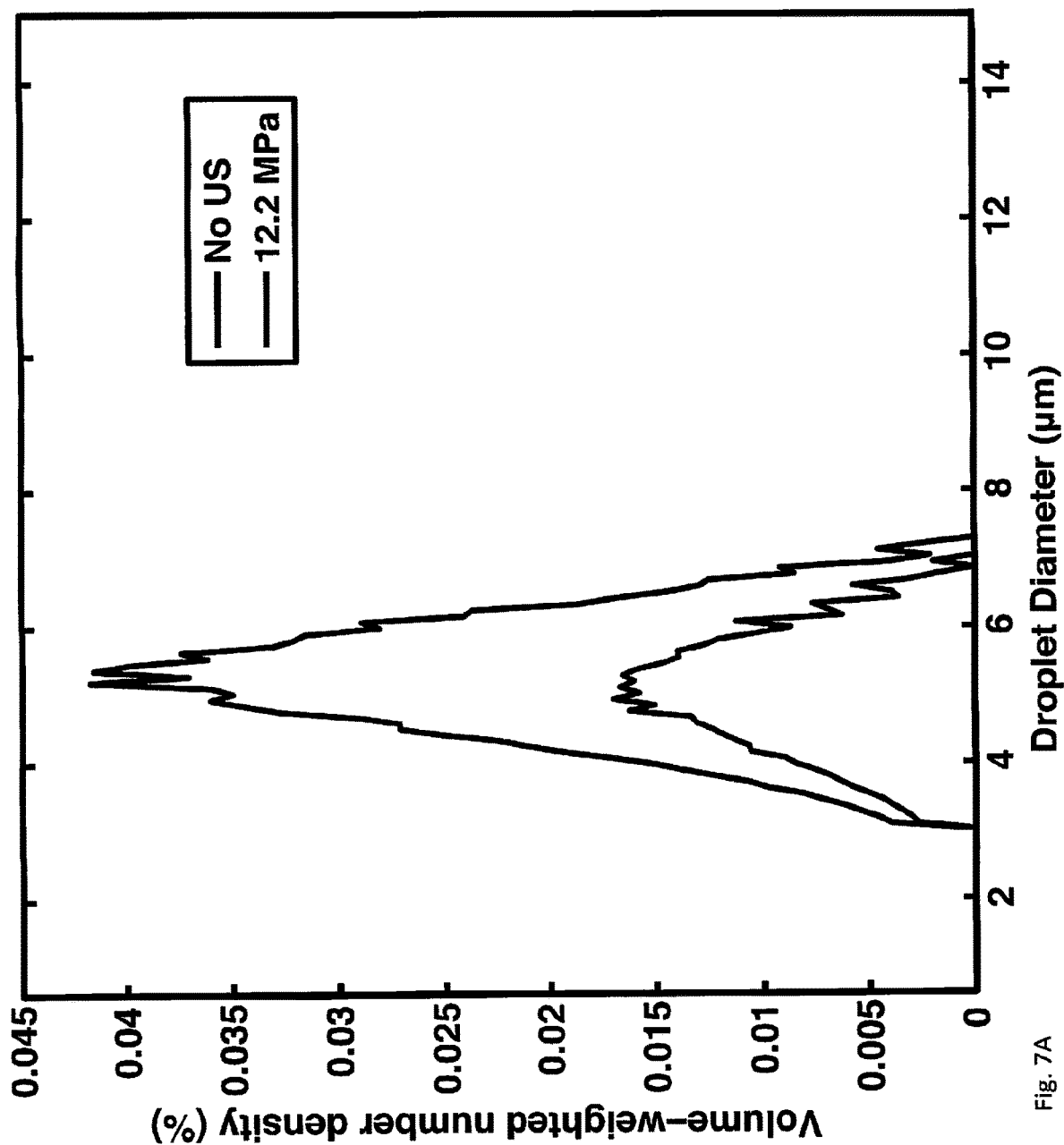
FIG. 7A shows the computed volume-weighted size distribution is shown without ultrasound exposure (black line) and after exposure to 12.2 MPa peak rarefactional pressure (red line). The size distributions (measured and computed) are normalized by the total volume of the PFP droplets without ultrasound exposure. The size distributions were obtained by applying a Gaussian probability density function with a mean and standard deviation of 5.6±2 µm to the centrifuged droplet distributions shown in FIG. 6A.
Figure 7B:
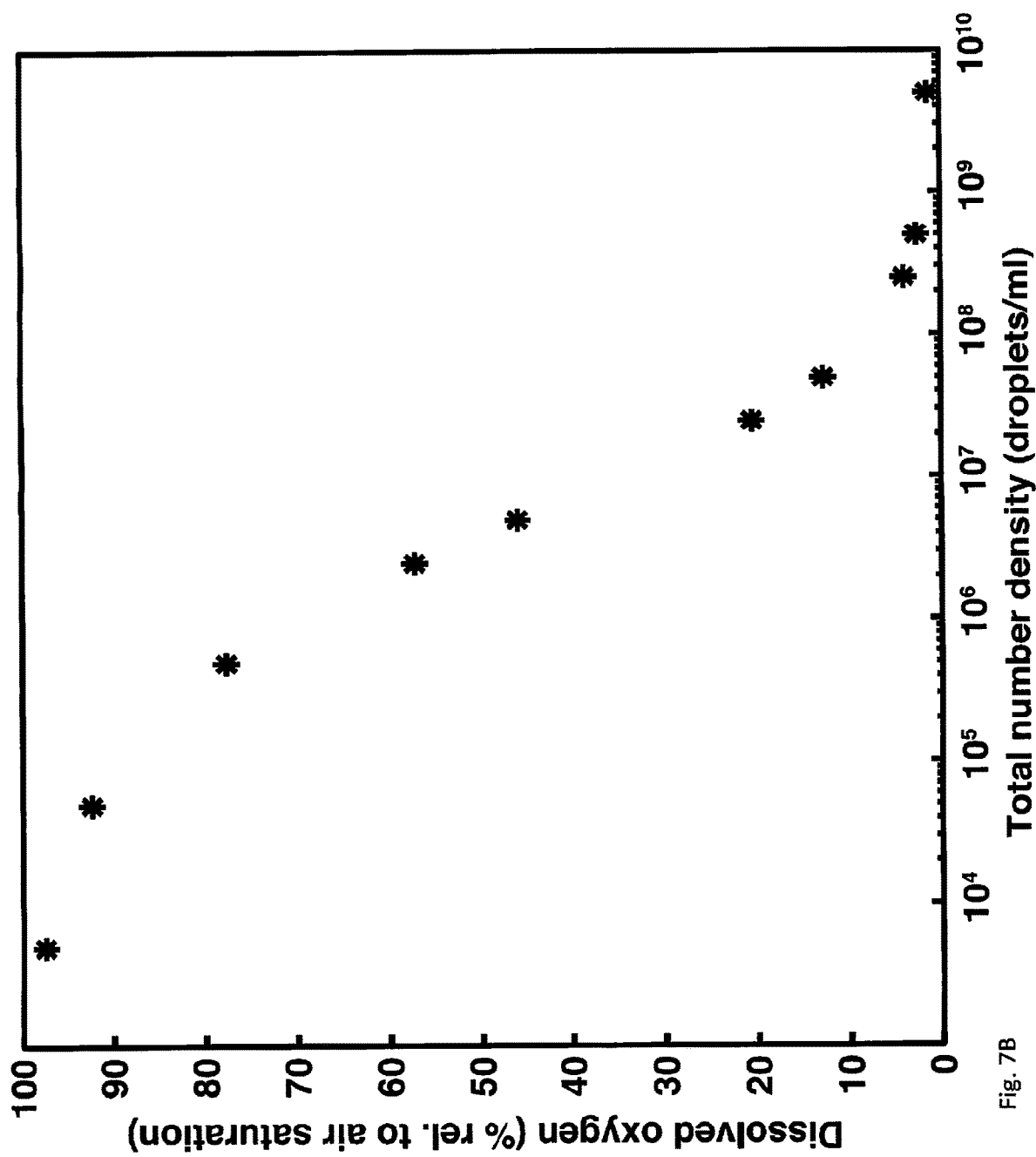
FIG. 7B shows the predicted dissolved oxygen is shown as a function of the concentration of the computed size distribution. Using this computed size distribution, the mathematical model (equation 6) yielded a predicted decrease in dissolved oxygen of 46% with an initial concentration of $4.98 \times 10^6$ droplets/ml.

FIG. 5A shows the number density of the capillaries in a human lung as measured by Hogg et al. This number density was used to compute the cumulative probability density function of droplets passing through the lung capillaries. The calculated volume-weighted number-density size distribution of PFP droplets after passing through the lung capillaries is shown in FIG. 5B. Only 54% of the PFP volume is predicted to pass through the lungs for non-centrifuged droplets while 86% of the PFP volume is predicted to pass through the lungs for centrifuged droplets.

FIG. 6A shows the volume-weighted number-density size distribution of the centrifuged droplets in the effluent without ultrasound insonation and after 12.2 MPa peak rarefactional pressure insonation. The droplets were insonified at 12.2 MPa to minimize the number of surviving droplets and maximize the decrease in dissolved oxygen. FIG. 6B shows the corresponding measured and predicted DO in the surrounding fluid. The DO in the fluid surrounding the centrifuged droplets upstream of the ultrasound insonation was 93±3%. The downstream DO in the fluid surrounding the centrifuged droplets after exposure to ultrasound with a 12.2 MPa peak rarefactional pressure was 39±4% (FIG. 6B). The measured and predicted DO values were not statistically significantly different.

Centrifugation of the droplets removed all but 14% of the PFP volume that would not be expected to pass through the pulmonary capillaries. This PFP volume corresponded to $8.4\times10^6$ centrifuged droplets. If each of these large droplets were to occlude the blood flow to a single alveoli, approximately 3% of the alveoli would be affected. However, each alveolus is fed by a network of capillary segments and it is unlikely that a single droplet would occlude a single alveolus. The largest sized droplets within a centrifuged emulsion depends on the centrifugation speed and duration. An optimal size distribution of centrifuged droplets could be found which would enable a higher percentage of droplets to pass through the pulmonary capillaries.

As shown in FIG. 6B, the centrifuged droplets without ultrasound exposure did not cause a significant decrease in the DO of the surrounding fluid, whereas non-centrifuged droplets without ultrasound exposure did cause a significant decrease in the DO of the surrounding fluid (FIG. 4). Droplets with diameters greater than 5 μm, which have a greater tendency to undergo spontaneous vaporization due to lower Laplace pressures, were filtered out through the centrifugation process (FIG. 5B).

The DO after 12.2 MPa peak rarefactional pressure insonation of centrifuged droplets was 39±4% which was higher than the DO after insonation of non-centrifuged droplets at the same pressure amplitude (22±4%). By keeping the total number density of droplets injected in the flow phantom approximately the same ($4\times10^8$ droplets/ml) for centrifuged and non-centrifuged droplets, the total volume of PFP in the injection and thus the total volume of PFP converted to a gas was not the same. The total volume of PFP converted to gas microbubbles dictates the change in dissolved oxygen (Equation 6). Despite the absence of these large droplets and microbubbles in the centrifuged emulsion, which scavenge significant amounts of oxygen, a greater than 40% decrease in DO in the surrounding fluid was observed. The size distribution of the droplets plays an important role in the amount of DO scavenged from the fluid during ADV.

2.4 Effect of Concentration of Droplets on DO in Fluid

FIG. 7A shows the computationally modified size distributions that were obtained after applying a Gaussian probability density function with a mean and standard deviation of 5.16±2 μm to the centrifuged droplet distributions without ultrasound exposure and after 12.2 MPa peak rarefactional ultrasound exposure (FIG. 6A). These size distributions were normalized by the total volume of PFP without ultrasound exposure. These volume-weighted size distributions were multiplied by a range of total number densities of droplets and used to compute the change in dissolved oxygen in the surrounding fluid as a function of droplet density (FIG. 7B). Using a total number density of $4.9\times10^6$ droplets/ml, the predicted DO was 46%. The predicted DO after ultrasound exposure decreases with an increasing number of droplets as shown in FIG. 7B.

Note that in this study the total number density of centrifuged and non-centrifuged droplets used in the flow system was $4.95\pm0.04\times10^8$ droplets/ml and $4.09\pm0.06\times10^8$ droplets/ml. Previous in vitro studies used droplets formulated employing the same methods as the current study with concentrations ranging from $3\times10^5$ droplets/ml to $7\times10^7$ droplets/ml. The concentration of droplets in previous ADV in vivo studies ranged from $6.5\times10^5$ droplets/ml to $1.4\times10^6$ droplets/ml, based on dividing the total number of droplets injected by the total blood volume of the animal. The FDA-approved in vivo concentrations of the perfluorocarbon-based ultrasound contrast agents Definity® and Optison® are $5\times10^6$ microbubbles/ml and $1.4\times10^6$ microbubbles/ml, respectively. We note that the size distribution of Definity® is similar but not the same as the size distribution of the droplets used in this study. These concentrations are based on the total bolus injection of microbubbles divided by the total blood pool volume. Thus the concentration of PFP droplets used in the current study is two orders of magnitude higher than previous in vitro and in vivo studies. A significant fraction of the total number of droplets used in this study did not contribute to a change in the DO of the surrounding fluid because they did not vaporize. Less than 10% of droplets smaller than 2 μm were converted into microbubbles with a 12.2 MPa peak rarefaction pressure insonation, yet these droplets contributed to more than 85% of the total number density of droplets. These non-activated droplets (<2 μm) could be removed from the emulsion to reduce the total number of droplets that would be injected in vivo. Either microfluidic techniques or differential centrifugation could be employed to achieve such an optimal size distribution.

Because such size isolation techniques have not yet been fully developed for PFP droplets, a numerical approach was used to identify an appropriate size distribution of the droplets which, when used at a concentration of at most $5\times10^6$ droplets/ml, would induce at least a 50% reduction in DO during ADV. Based on these constraints, the size distribution curve shown in FIG. 7A would be suitable for scavenging DO from the surrounding fluid via ADV in intravascular applications. To emphasize the importance of size isolation, a droplet concentration of $4\times10^8$ droplets/ml for the size distribution shown in FIG. 7A would yield a predicted scavenged DO of 3%. In comparison, the DO predicted using the size distribution of the centrifuged droplets (FIG. 6A) with a concentration of $4\times10^8$ droplets/ml was 39%.

Additionally, the decrease in DO due to ADV was estimated for previous in vitro studies as 95% and 50% based on droplet concentrations of $3\times10^5$ droplets/ml and $7\times10^7$ droplets/ml, respectively. The estimated DO decrease in previous in vivo studies was 91% and 80% based on droplet concentrations of $6.5\times10^5$ droplets/ml and $1.4\times10^6$ droplets/nil, respectively. The droplet size distribution in these previous studies was assumed to be similar to that in the current study because the same droplet manufacturing protocol was used. The DO estimation also assumes that the ADV transition efficiency in these studies was similar to that in the current study. However, the transition efficiency, and thus the amount of scavenged oxygen, is dependent on ultrasound insonation parameters such as pressure amplitude, frequency, and pulse duration. Therefore the actual changes in DO in those experiments may be different.

2.5 Role of Ultrasound Parameters in Droplet Conversion

The ultrasound parameters used in this study were not particularly effective at transitioning the phase of the droplets. Only approximately 40% of the 5 μm droplets were transitioned with a 12.2 MPa peak rarefactional pressure amplitude (FIG. 3B). It was observed that increasing the ultrasound insonation pressure amplitude increased the fraction of droplets transitioned (FIG. 3B). To scavenge additional oxygen, the ultrasound insonation parameters could be modified. Larger pressure amplitudes are required for lower frequency ultrasound exposure to convert the droplets to microbubbles. Additionally, smaller droplets require larger pressure amplitudes to transition and a lower percentage of the droplets undergo a phase transition. Increasing the pulse duration or simultaneously administering a perfluorocarbon-based ultrasound contrast agent has also been shown to lower the transition threshold and likely would increase the transition efficiency.

2.6 Potential Fate of Scavenged Oxygen In Vivo

Eventually the microbubbles with scavenged oxygen will dissolve, releasing the oxygen back into the blood where it would likely either bind to hemoglobin or increase the dissolved oxygen content of plasma. This dissolution is anticipated to happen on a time scale of tens of seconds. Blood circulates through the adult human body approximately once per minute. As the blood circulates through the pulmonary capillary bed, the dissolved oxygen in the blood would return to normal oxygen levels and the perfluoropentane microbubbles would be exhaled similar to the excretion of other perfluorocarbon-based ultrasound contrast agent gases.

2.7 Conclusion

Local scavenging of dissolved oxygen from a fluid via acoustic droplet vaporization of a perfluoropentane emulsion was quantified in an in vitro flow phantom. The predicted change in dissolved oxygen using a simple numerical model based on conservation of mass and isobaric partial pressures agreed with the dissolved oxygen measurements (p-values were equal to 0.32, 0.18, and 0.95 for 2.5 MPa, 7.3 MPa, and 12.2 MPa insonations, respectively). The data suggest that the mechanism of gas manipulation is based on dissolved gas concentration gradients, which would likely occur for other important dissolved gases, such as nitrogen and carbon dioxide. The volume of perfluoropentane phase transition dictates the amount of dissolved oxygen scavenged from a fluid. The acoustic peak rarefactional pressure and the volumetric size distribution and concentration of the droplets all affect the volume of perfluoropentane undergoing phase transition. The scavenging effect was rapid with dissolved oxygen decreasing from 100% air saturation to approximately 22% of air saturation in less than 20 seconds in a 5 ml/min flow.

The invention claimed is:

1. A method of treating a patient for a condition characterized by an excess blood concentration of dissolved gas in at least one targeted region of the patient, the method comprising: administering a composition comprising a perfluorocarbon (PFC) droplet emulsion into the blood of the patient; insonifying the at least one target region sufficient to achieve formation of microbubbles by droplet vaporization of at least a portion of the perfluorocarbon droplets present in the blood; whereby a concentration gradient favoring movement of gas molecules from the blood into the microbubbles is established for a time frame.

2. The method according to claim 1, wherein the condition being treated is decompression sickness and the gas comprises nitrogen.

3. The method according to claim 1, wherein the condition being treated is a pH-related biological condition and the gas comprises carbon dioxide.

4. The method according to claim 3, wherein the condition comprises acidosis.

5. The method according to claim 1, wherein the condition being treated is selected from oxygen toxicity and reperfusion injury and the gas comprises oxygen.

6. The method according to claim 1, wherein the condition being treated is carbon monoxide poisoning and the gas comprises carbon monoxide.

7. The method according to claim 1, further comprising preparing the PFC droplet emulsion prior to the step of administration, wherein preparing comprises generating size-isolated PFC droplets.

8. The method according to claim 7, wherein size-isolated PFC droplets are generated by differential centrifugation.

9. The method according to claim 7, wherein the size of the generated PFC droplets ranges from 0.3 μm to about 100 μm.

10. The method according to claim 7, wherein the size of the generated PFC droplets ranges from about 2 μm to about 5 μm diameter.

11. The method according to claim 1, wherein insonifying comprises administering ultrasound to the target at or above a threshold pressure amplitude, wherein threshold is defined as a minimum pressure amplitude necessary to transition the droplets.

12. The method according to claim 11, wherein the insonifying comprises administering from between 500 kHz to 10 MHz ultrasound and ultrasound is administered at a pressure amplitude between the threshold pressure and 5 MPa.

13. The method according to claim 12, wherein the insonifying comprises administering 2 MHz ultrasound and the threshold pressure amplitude is about 1.7 MPa.

14. The method according to claim 1, wherein the time frame is between 10 milliseconds and 60 seconds.

15. The method according to claim 14, wherein the time frame is approximately 20 seconds.

16. The method according to claim 1, wherein the dissolved gas is oxygen and a percent dissolved oxygen ($DO_1$) in the blood of the patient after insonification is predicted according to an equation:

$$DO_l = \frac{kn_l}{V_l P_{l0}} \times DO_{l0}$$

wherein
k=Henry's constant for oxygen in water;
$n_f$=number of moles of oxygen in blood surrounding the PFC droplets;
$V_f$=volume of the blood surrounding the PFC droplets;
$P_{f0}$=initial partial pressure of oxygen in the blood surrounding the PFC droplets; and
$DO_{f0}$=initial dissolved oxygen in the blood surrounding the PFC droplets.

17. The method according to claim 1, further comprising monitoring the treatment using imaging technology.

* * * * *